United States Patent [19]

Los

[11] Patent Number: 4,554,013

[45] Date of Patent: Nov. 19, 1985

[54] HERBICIDAL IMIDAZOLINYL NAPHTHOIC ACIDS

[75] Inventor: Marinus Los, Pennington, N.J.

[73] Assignee: American Cyanamid Company, Stamford, Conn.

[21] Appl. No.: 631,283

[22] Filed: Jul. 16, 1984

Related U.S. Application Data

[63] Continuation-in-part of Ser. No. 519,616, Aug. 2, 1983, abandoned.

[51] Int. Cl.$^4$ .................. A01N 43/50; C07D 233/70
[52] U.S. Cl. ........................................ 71/92; 548/301
[58] Field of Search ............................ 548/301; 71/92

[56] References Cited

U.S. PATENT DOCUMENTS 4,170,642 10/1979 O'Neal ........................... 548/301 X
4,188,487 2/1980 Los ..................................... 548/301

OTHER PUBLICATIONS

Hofmann, K., *Imidazole and its Derivatives*, Part I, Interscience, New York, 1953, pp. 95–97.

*Primary Examiner*—Richard A. Schwartz
*Attorney, Agent, or Firm*—H. G. Jackson

[57] ABSTRACT

The present invention relates to novel herbicidally active substituted imidazolinyl benzoic acids, esters and salts and a method for the preparation thereof. The invention also relates to a method for controlling undesirable monocotyledonous and dicotyledonous plant species therewith.

9 Claims, No Drawings

HERBICIDAL IMIDAZOLINYL NAPHTHOIC ACIDS

This application is a continuation-in-part of Ser. No. 519,616, filed Aug. 2, 1983, now abandoned.

The present invention relates to novel herbicidally active substituted imidazolinyl benzoic acids, esters and salts and a method for the preparation thereof. The invention also relates to a method for controlling undesirable monocotyledonous and dicotyledonous plant species therewith.

More particularly, the present invention relates to herbicidally effective, substituted imidazolinyl benzoic acids, esters and salts represented by the structure:

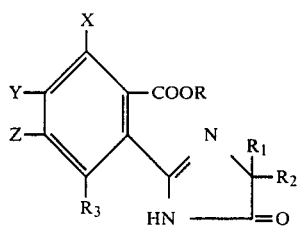

wherein
R is hydrogen;
$C_1$–$C_{12}$ alkyl optionally substituted with one of the following groups: $C_1$–$C_4$ alkoxy, halogen, hydroxyl, $C_3$–$C_6$ cycloalkyl, benzyloxy, furyl, phenyl, halophenyl, $C_1$–$C_4$ alkylphenyl, $C_1$–$C_4$ alkoxyphenyl nitrophenyl, carboxyl, $C_1$–$C_3$ alkoxycarbonyl, cyano or tri($C_1$–$C_3$)alkylammonium;
$C_3$–$C_{12}$ alkenyl optionally substituted with one of the following groups: $C_1$–$C_3$ alkoxy, phenyl, halogen, or $C_1$–$C_3$ alkoxycarbonyl or with two $C_1$–$C_4$ alkoxy groups or two halogen atoms;
$C_3$–$C_6$ cycloalkyl optionally substituted with one or two $C_1$–$C_3$ alkyl groups;
$C_3$–$C_{10}$ alkynyl; or,
a cation;
$R_1$ and $R_2$ each represent $C_1$–$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$–$C_6$ cycloalkyl ring optionally substituted with methyl;
X is hydrogen, halogen or methyl;
Y and Z are each hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, $OCF_2CHF_2$, $OCF_3$, $OCHF_2$, nitro, cyano, $C_1$–$C_4$ alkylsulfonyl, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one or two $C_1$–$C_4$ alkyl, $C_1$–$C_4$ alkoxy or halogen or combinations of any two of these groups;
$R_3$ is hydrogen, halogen, $C_1$–$C_4$ alkyl, $C_1$–$C_4$ alkylthio, $C_1$–$C_4$ alkoxy, $CF_3$, $NO_2$, $OCF_3$, $OCHF_2$ or $OCF_2CHF_2$;
$R_4$ is hydrogen or $C_1$–$C_4$ alkyl;
$R_5$ is $C_1$–$C_4$ alkyl;
And, when taken together, Y and Z may form a ring in which YZ is represented by (1) the structure: —$(CH_2)_n$—, where n is an integer of 2, 3 or 4; or
(2) by the structure:

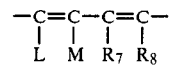

where L, M, $R_7$ and $R_8$ each represent hydrogen, halogen, $C_1$–$C_4$ alkyl or $C_1$–$C_3$ alkoxy;
and when $R_1$ and $R_2$ are not the same, the optical isomers thereof and except when R is a cation, the acid addition salts thereof; with the proviso that when three of the substituents represented by X, Y, Z and $R_3$ are hydrogen, the remaining X, Y, Z or $R_3$ are $R_3$ substituent cannot be hydrogen, halogen, $C_1$–$C_3$ alkyl or nitro.

As used in the present specification and claims, the term "halogen" means F, Cl, Br or I. unless otherwise specified.

Examples of the R cation are alkali metals, alkaline earth metals, manganese, copper, iron, zinc, cobalt, lead, silver, nickel, ammonium or organic ammonium. The alkali metals include: sodium, potassium and lithium, although sodium is generally preferred. Also, in the present specification and claims, unless otherwise specified, the term "organic ammonium" is defined as a group consisting of a positively charged nitrogen atom joined to from one to four aliphatic groups, each containing from one to 20 carbon atoms. Among the organic ammonium groups which are illustrative for the preparation of the aliphatic ammonium salts of the imidazolidinyl acids of formulas I through VIII are: monoalkylammonium, dialkylamonium, trialklammonium, tetraalkylammonium, monoalkenylammonium, dialkenylammonium trialkenylammonium, monoalkynylammonium, dialkynylammonium, trialkynylammonium, monoalkanolammonium, dialkanolammonium, trialkanolammonium, $C_5$–$C_6$ cycloalkylammonium, piperidinium, morpholinium, pyrrolidinium, benzylammonium and equivalents thereof.

Although a variety of herbicidally active imidazolinyl benzoic acids, esters, and salts, are described in U.S. Pat. No. 4,188,487 issued Feb. 20, 1980, still more effective herbicidal agents would be useful to farmers, agriculturists, industrialists and the like for the control of undesirable plant species.

It is therefore an object of the present invention to provide novel, more effective, imidazolinyl benzoic acids, esters and salts for inhibiting or eliminating undesirable plant species, such as bindweed, quackgrass and wild oats, which are generally difficult to control or eradicate with presently available herbicidal agents.

The novel, herbicidally active, substituted 2-(2-imidazolidinyl)benzoic acids, esters and salts of the present invention, represented by the structure:

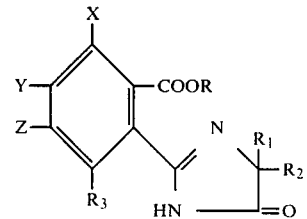

where R, $R_1$, $R_2$, $R_3$, W, X, Y and Z are as described above, can be prepared by reaction of an appropriately substituted formula XV benzoic acid with thionyl chloride and a catalytic amount of dimethylformamide. The mixture is admixed with an anhydrous aromatic solvent such as toluene, xylene or the like, and the solvent evaporated. The remaining residue is then diluted with an anhydrous non-protic solvent such as tetrahydrofuran and the resulting mixture admixed with a solution of a di($C_1$–$C_3$)alkylamine in anhydrous non-protic solvent. This reaction is preferably conducted under a blanket of inert gas at a temperature between about −10° and +10° C. and yields the formula XVI, substituted N,N-di($C_1$–$C_3$)alkylbenzamide. The formula XVI substituted benzamide is thereafter treated with sec-butyl lithium in an anhydrous non-protic solvent such as tetrahydrofuran (THF) in the presence of N,N,N′,N′-tetramethylethylenediamine (TMEDA). The reaction mixture is preferably maintained under a blanket of inert gas, such as nitrogen, at a temperature between about −75° and −65° C. Thereafter, the reaction mixture is admixed with anhydrous THF saturated with carbon dioxide, then mixed with water. The aqueous phase is separated, cooled to between 0° and 10° C. and acidified to yield the formula XVII substituted phthalic acid. These reactions may be illustrated as follows:

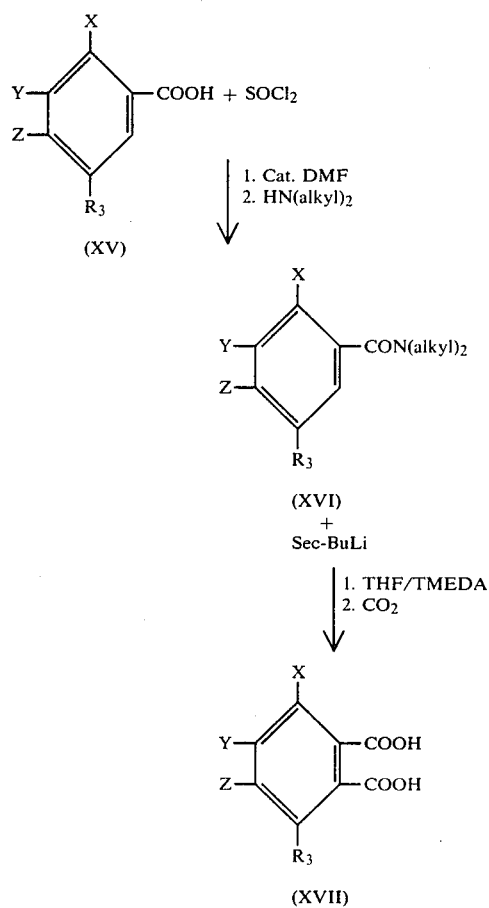

wherein X, Y, Z, and $R_3$ are as described above.

The formula XVII substituted phthalic acid is treated with an excess of acetic anhydride, heated to refluxing temperature and concentrated in vacuo with anhydrous aromatic solvent such as toluene, xylene or the like, to obtain the substituted phthalic anhydride of formula XVIII. The substituted phthalic anhydride is then dissolved in anhydrous non-protic solvent such as THF and treated with an equimolar amount of a formula XIX α-aminocarbonitrile such as 2-amino-2,3-dimethylbutyronitrile and a trialkylamine such as triethylamine or trimethylamine at a temperature between about 20° and 30° C. Thereafter, the solvent is removed and the remaining residue heated to refluxing temperature in an excess of acetic anhydride to yield the substituted 1,3-dioxo-2-isoindolinealkylnitrile of formula XXI.

Alternatively, the formula XVIII substituted phthalic anhydride may be reacted with an equimolar amount of a formula XIX substituted α-aminocarbonitrile by heating the mixture to refluxing temperature in the presence of a chlorinated hydrocarbon solvent such as ethylene chloride, methylene chloride, dichloroethane or the like, to yield an isomeric mixture of the formula XXa and XXb monoamides of phthalic acid. The thus-formed acids may then be cyclized to the substituted 1,3-dioxo-2-isoindolinealkylnitrile depicted by formula XXI, by heating the reaction mixture to between about 20° and 100° C., with an excess of acetic anhydride, preferably in the presence of a catalytic amount of sodium acetate or potassium acetate. Hydration of the thus-formed substituted 1,3-dioxo-2-isoindolinealkylnitrile formula XXI is carried out by treating said formula XXI nitrile with a strong acid such as sulfuric acid containing a small amount of water. This reaction yields the formula XXII substituted 1,3-dioxo-2-isoindolinealkylamide and is generally conducted at a temperature between about 30° and 60° C. After heating, the mixture may be poured over ice and extracted with a chlorinated hydrocarbon such as chloroform, methylene chloride or the like. The solvent is then removed preferably by concentration in vacuo. Ring opening of the formula XXII substituted 1,3-dioxo-2-isoindolinealkylamide is achieved by treatment thereof with an equimolar amount of sodium methoxide in the presence of a lower alkyl alcohol, preferably at a temperature between about 20° and 30° C. The reaction mixture is thereafter neutralized to pH 7 with acetic acid to yield an isomeric mixture of the carbamoyl phthalamic acid esters illustrated by formulas XXIIIa and XXIIIb. Cyclization of the carbamoyl phthalamic acid esters can then be achieved by reaction thereof with approximately a 2-molar equivalent excess of phosphorous pentachloride in the presence of anhydrous toluene at a temperature between about 20° and 30° C. The reaction mixture is poured over ice to give the hydrochloride salt of the corresponding 2-(2-imidazolin-2-yl)benzoate depicted by formulas XXIVa and XXIVb. Treatment of the formulas XXIVa and XXIVb hydrochlorides with one equivalent of a base such as an alkali metal bicarbonate, carbonate hydroxide then gives the methyl benzoates as depicted in formulas XXIVa and XXIVb.

The above reactions are graphically illustrated in Flow Diagram I below.

FLOW DIAGRAM I
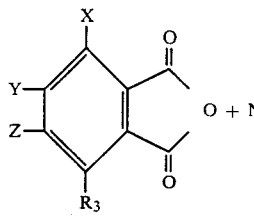 + 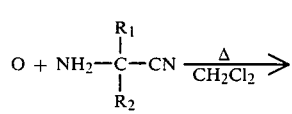
(XVIII)         (XIX)
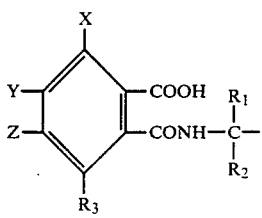 + 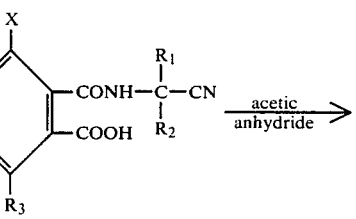 acetic anhydride →
(XXa)           (XXb)
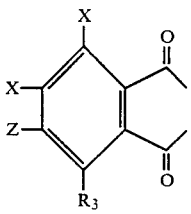 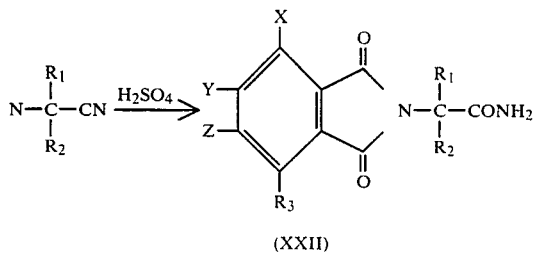
(XXI)           (XXII)
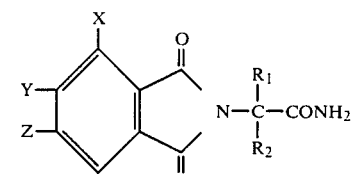
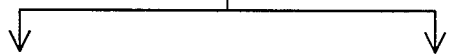
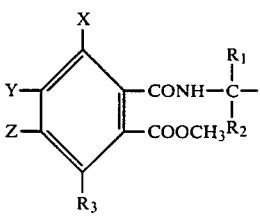   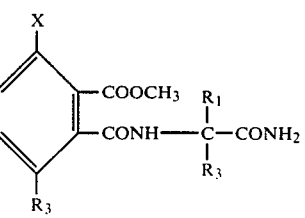
(XXIIIa)           (XXIIIb)
1. $PCl_5$           1. $PCl_5$
2. Base              2. Base

FLOW DIAGRAM I

-continued

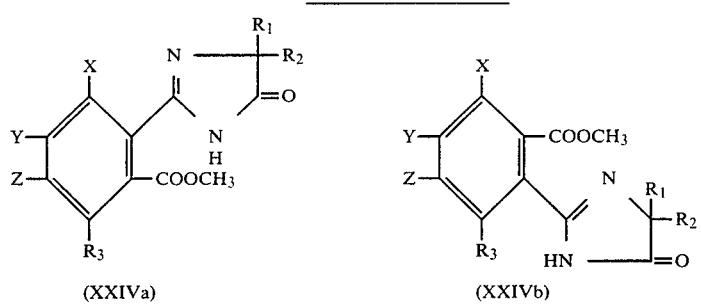

(XXIVa)    (XXIVb)

A preferred method for preparing the formula XXVIIIa and XXVIIIb substituted (5-oxo-2-imidazolin-2-yl)benzoic acids, involves the preparation of the substituted or unsubstituted formula XVIII phthalic anhydride by reaction of a formula XVII substituted or unsubstituted phthalic acid with acetic anhydride, dimethoxyethane and pyridine. The thus-prepared phthalic anhydride of formula XVIII is then admixed with an equivalent amount of a formula XXVI carboxamide, in the presence of an inert organic solvent such as a low-boiling ether (diethyl ether, tetrahydrofuran, dimethoxyethane) acetonitrile, ethyl acetate or a halogenated hydrocarbon, at a temperature between 20° and 60° C. and preferably 25° to 30° C. under a blanket of inert gas such as nitrogen. When the reaction is essentially complete, the product is isolated by convenient means, e.g., filtration, distillation of the solvent or by extraction into aqueous base if the solvent is water immiscible. The reaction yields the isomeric phthalamic monoacid/monoamide products, formulas XXVIIa and XXVIIb.

The thus-formed mixture is then heated to about 25° to 100° C., with about 2 to 10 molar equivalents of aqueous alcoholic sodium or potassium hydroxide. The reaction is preferably conducted under a blanket of inert gas, such as nitrogen. If the product is insoluble in water, it will precipitate from the aqueous phase and be recovered by filtration or extraction. If the product is soluble in water, the mixture can be extracted with an organic solvent such as ether, methylene chloride or the like, and the extract concentrated to provide an isomeric mixture of the formula XXVIIIa and XXVIIIb substituted 2-(5-oxo-2-imidazolin-2-yl)benzoic acids with compounds of formula XXVIIIa and XXVIIIb. The above reactions are graphically illustrated in Flow Diagram II below.

FLOW DIAGRAM II

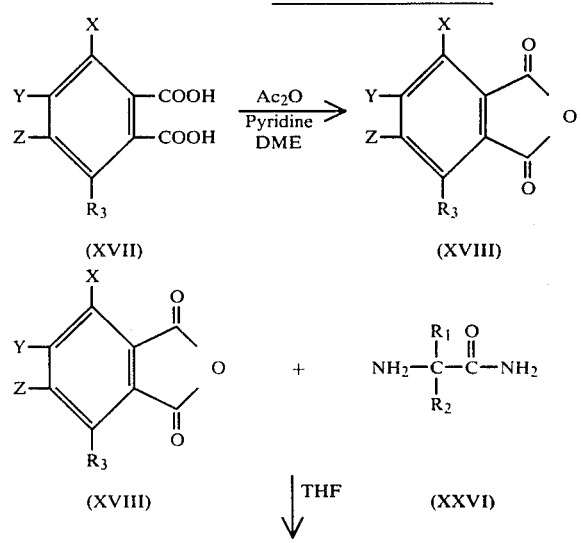

FLOW DIAGRAM II

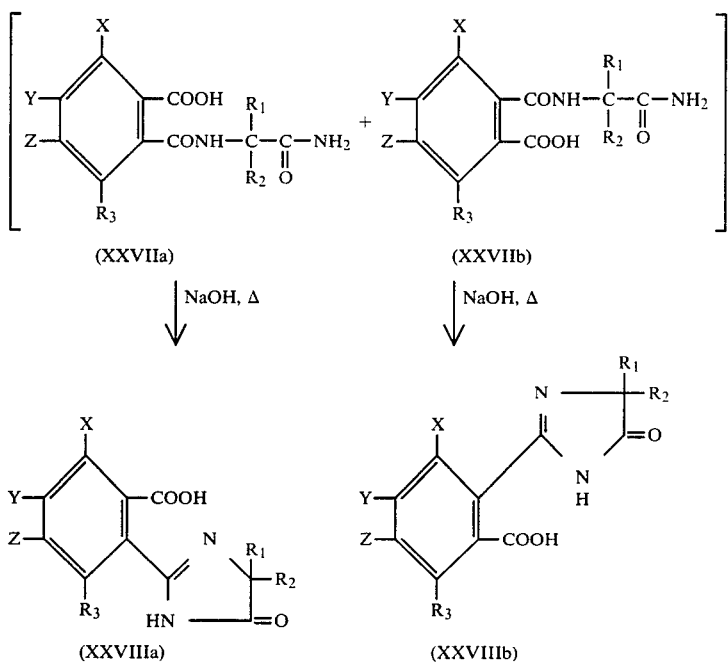

From the above discussions, it can be seen that many synthetic routes to the 2-(2-imidazolidinyl)benzoic acids and/or esters yield mixtures of the herbicidally effective acid or ester isomers. While these isomeric mixtures have been found to be very effective for the selective control of undesirable plant species, it has also been determined that, not infrequently, one of the isomers is somewhat more effective and/or selective than the other. Thus, it is sometimes desirable to direct a synthesis to a single isomer.

As an example of a synthetic route to a single isomer, formula XXIX, 3-nitrophthalic anhydride, may be dispersed or dissolved in an excess of $C_1$–$C_3$ alcohol and heated to refluxing temperature, generally between about 60° and 100° C. After refluxing, the alcohol is evaporated in vacuo and the residue recrystallized from ethyl acetate to yield the ring-opened formula XXX, 2-alkyl 3-nitrophtalate. The formula XXX compound is then dispersed in thionyl chloride and the resulting mixture maintained at a temperature between about 20° and 40° C. until the reaction is essentially complete. The mixture is concentrated and the residue taken up in an aromatic solvent such as toluene and concentrated again to yield the formula XXXI alkyl 2-(chlorcarbonyl)-6-nitrobenzoate. This formula XXXI nitrobenzoate is then admixed with about an equimolar amount of a formula XIX substituted α-aminocarboxamide and heated to refluxing temperature in the presence of a non-protic solvent such as tetrahydrofuran and a trialkylamine to yield the formula XXXII, carbamoyl-6-nitrophthalamate. Cyclization of said formula XXXII carbamoyl-6-nitrophthalamate to the formula XXXIII 2-(2-imidazolin-2-yl)-6-nitrobenzoate can then be achieved with phosphorus pentachloride at an elevated temperature, generally between 60° and 100° C. The reaction is preferably conducted in the presence of an inert organic solvent, such as toluene or benzene. The above reactions are graphically illustrated in Flow Diagram III below.

FLOW DIAGRAM III

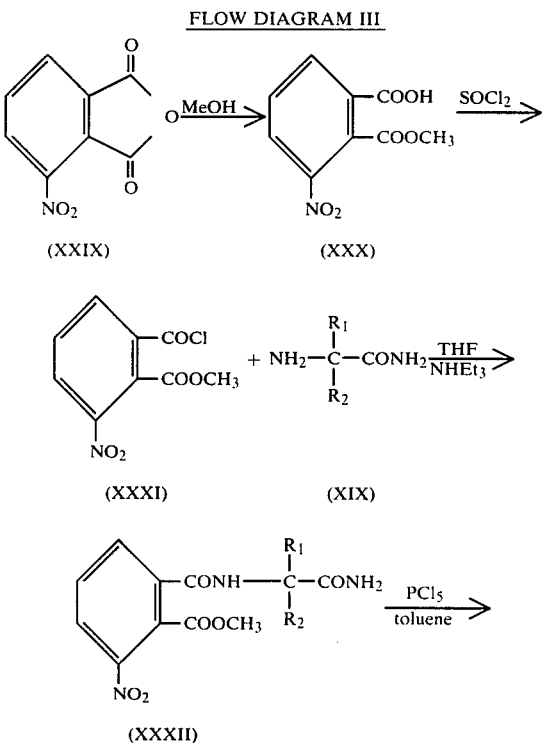

FLOW DIAGRAM III -continued

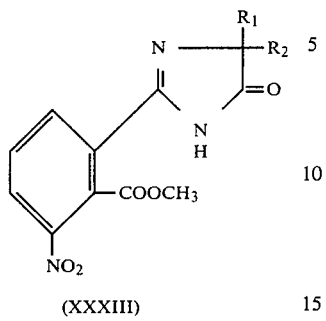

(XXXIII)

Another method for preparing mono-substituted and multi-substituted 2-(2-imidazolinyl)benzoic acids and esters, involves the reaction of a formula XV, substituted benzoic acid with thionyl chloride and a catalytic amount of dimethylformamide to give the formula XXXIV substituted benzoylchloride. The reaction is preferably heated to between 25° and 40° C. and then evaporated in vacuo with an anhydrous aromatic solvent such as toluene, to give the substituted benzoyl chloride. The thus obtained substituted benzoyl chloride is then admixed with equimolar amounts of a formula XXVI carboxamide and a trialkylamine, such as triethylamine, triisopropylamine or the like, in the presence of an non-protic solvent such as tetrahydrofuran. During addition of the reactants, the reaction mixture is generally maintained at a temperature between about 0° and 15° C. When addition is complete, the mixture is allowed to warm to ambient temperature, then treated with water and extracted with an organic solvent such as ethyl acetate to obtain the N-substituted benzamide of formula XXXV. The thus-formed N-substituted benzamide is then heated to a temperature of from 25° to 110° C. with about 2 to 10 molar equivalents of aqueous or aqueous alcoholic sodium or potassium hydroxide, preferably under a blanket of inert gas such as nitrogen. The reaction yields the formula XXXVI substituted phenyl imidazolinone which can be converted to the corresponding substituted (5-oxo-2-imidazolin-2-yl) benzoic acid depicted by formula XXXVII, using sec-butyl lithium and carbon dioxide. This reaction is preferably carried out by dissolving or dispersing the formula XXXVI substituted phenyl imidazolinone in tetrahydrofuran or other non-protic solvent and about three equivalents of tetramethylenediamine under a blanket of inert gas such as nitrogen. The reaction mixture is maintained at a temperature between about −70° and −50° C. and then treated with a solution of sec-butyl lithium in cyclohexane. Thereafter the reaction mixture is admixed with tetrahydrofuran saturated with carbon dioxide to yield the formula XXXVII substituted (5-oxo-2-imidazolin-2-yl)benzoic acid. These reactions are illustrated graphically in Flow Diagram IV below.

FLOW DIAGRAM IV

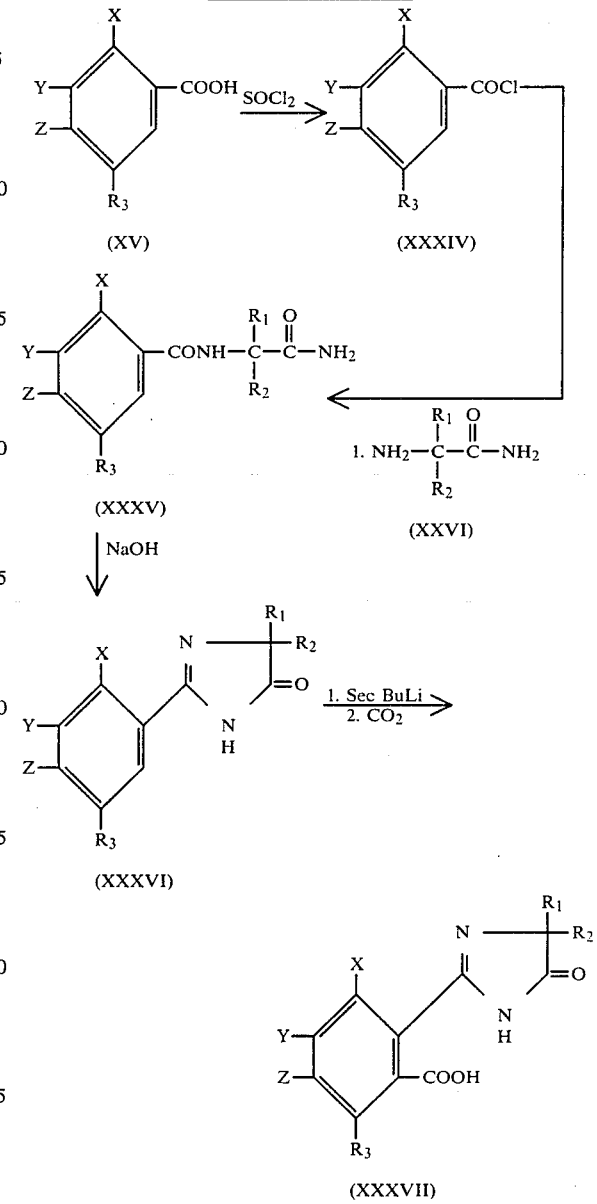

Alternatively, the formula XV substituted benzoic acid may be converted to the formula XXXIV benzoylchloride, as described above. Thereafter, the benzoylchloride is dispersed in tetrahydrofuran and admixed with a solution of 3 to 5 and preferably about 4 equivalents of diethylamine in tetrahydrofuran. Addition is generally conducted under a blanket of nitrogen while maintaining the temperature of the reaction mixture between about −10° and 0° C. The reaction yields the formula XXXVII substituted benzamide. The abovesaid substituted benzamide may then be dissolved in anhydrous tetrahydrofuran and treated with an equivalent amount of sec-butyl lithium dispersed in cyclohexane. This treatment is generally conducted under a blanket of nitrogen, while maintaining the temperature of the reaction mixture between about −70° and −50° C. Thereafter, the reaction mixture is admixed with anhydrous tetrahydrofuran saturated with carbon dioxide to yield the formula XXXIX substituted phthalamic acid. Treatment of a stirred solution of the substituted phthalamic acid in dry tetrahydrofuran with ethyl chloroformate followed by triethylamine and a solution of a formula XXVI carboxamide in anhydrous tetrahydrofuran, yields the substituted N,N-diethylphthalamide of formula XL. Base cyclization of the formula XL substituted N,N-diethylphthalamide can be achieved by heating said formula XL compound with from 2 to 10 molar equivalents of aqueous or aqueous alcoholic sodium or potassium hydroxide to a temperature between about 25° and 110° C., preferably under a blanket of nitrogen. This reaction yields the formula XLI substituted N,N-diethyl(5-oxo-2-imidazolin-2-yl)benzamide, which is readily converted to the corresponding acid of formula XLIII by heating with a concentrated mineral acid such as concentrated hydrochloric or hydrobromic acid. After acidification, the mixture is cooled, basified to a pH between 7 and 10, with alkali metal hydroxide, such as sodium hydroxide or potassium hydroxide and then carefully acified to pH 3 with concentrated sulfuric acid. The formula XLI substituted N,N-diethyl(5-oxo-2-imidazolin-2-yl)benzamide salt also undergoes transesterification with methanol and hydrogen chloride, yielding the corresponding formula XLII methyl ester of the said formula XLI N,N-diethylbenzamide. Treatment of the formula XLII substituted methyl (5-oxo-2-imidazolin-2-yl)benzoate with aqueous or aqueous alcoholic alkali metal hydroxide at an elevated temperature between about 60° and 100° C., followed by acidification with hydrochloric acid then yields the formula XLIII substituted (5-oxo-2-imidazolin-2-yl)benzoic acid. These reactions are illustrated in Flow Diagram IVa below.

FLOW DIAGRAM IVa

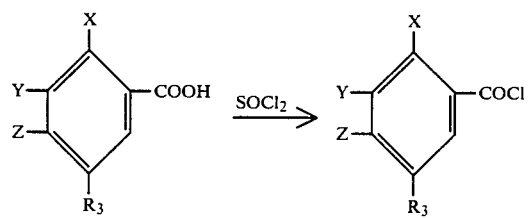

(XV) → (XXXIV)

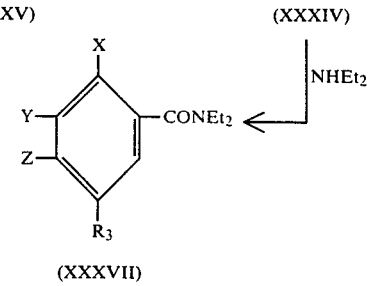

(XXXVII)

-continued

FLOW DIAGRAM IVa

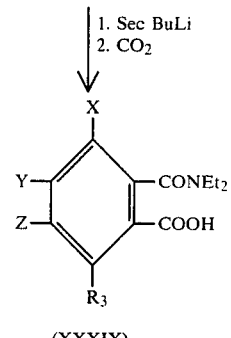

(XXXIX)

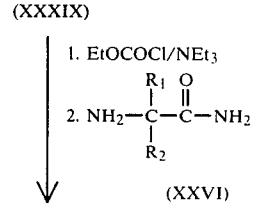

(XXVI)

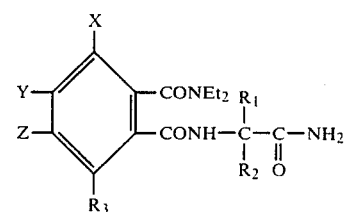

(XL)

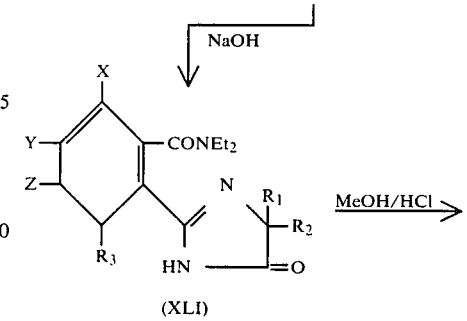

(XLI)

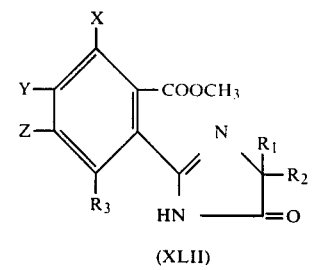

(XLII)

-continued
FLOW DIAGRAM IVa

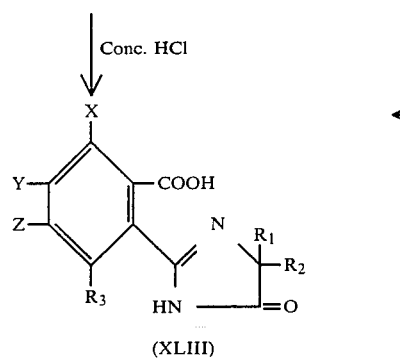

(XLIII)

An alternative process for the preparation of substituted 2-(5-oxo-2-imidazolin-2-yl)benzoic acids, involves the reaction of a substituted benzoyl chloride with a formula XXVI carboxamide in the presence of a trialkylamine and a solvent such as tetrahydrofuran, to obtain an N-substituted benzamide. This N-substituted amide is then heated to 25° to 110° C. with an excess of aqueous or aqueous alcohol sodium or potassium hydroxide to yield a formula XLIV substituted phenyl imidazolinone. These reactions are similar to the initial reactions described above and illustrated in Flow Diagram IV. However, where it is desirable to provide an additional $C_1$–$C_3$ alkyl substituent on the substituted ring of the above-mentioned formula XLIV, imidazolinone said imidazolinone may be dissolved in anhydrous tetrahydrofuran and treated with sec-butyl lithium, preferably dissolved in cyclohexane or other aromatic solvent. The addition of the sec-butyl lithium to the imidazolinone is preferably conducted over an extended period of time, up to several hours, while maintaining the reaction mixture at a temperature between about −50° and −75° C. When addition is complete, the reaction mixture is permitted to warm to between about −30° and −50° C. and then admixed with a $C_1$–$C_3$ alkyl iodide dispersed in tetrahydrofuran. After stirring the reaction mixture is allowed to warm to ambient temperature and then the solvent is evaporated in vacuo to obtain the formula XLV multi-substituted product. Reaction is graphically illustrated in Flow Diagram V, using methyl iodide and sec-butyl lithium for illustration.

Where it is desirable to provide a halogen substituent on the aromatic ring of the formula XLIV substituted imidazolinone said substituted imidazolinone is dissolved in an anhydrous non-protic solvent such as tetrahydrofuran and treated with sec-butyl lithium dissolved in cyclohexane. The addition is made over a period of from about 0.5 to 2.0 hours while maintaining the reaction mixture at a temperature below about −50° C. The mixture is then warmed to a temperature between about −30° and −40° C. and halogenated with a halogenating agent such as hexachloroethane or the like, preferably dispersed in an anhydrous non-protic solvent such as tetrahydrofuran. The mixture is then permitted to warm to ambient temperature treated with iced saturated brine and then acidified to pH 3 with a strong mineral acid. Thereafter, the formula XLVI halogenated product is extracted from the reaction mixture with an organic solvent such as ether. This formula XLVI halogenated imidazolinone is then readily converted to the corresponding formula XLVII, substituted 2-(5-oxo-2-imidazolin-2-yl)benzoic acid by reaction of said halogenated imidazolinone with sec-butyl lithium in the presence of tetrahydrofuran and tetramethylenediamine under a blanket of nitrogen, followed by admixture of the thus-prepared reaction mixture with anhydrous tetrahydrofuran, saturated with carbon dioxide. The formula XLVII product may be recovered from the reaction mixture by dispersing said mixture in water and acidifying the same with a strong mineral acid. The organic phase is then separated from the mixture and extracted with base. The aqueous phase is separated and acidified with mineral acid to yield the desired product. These reactions are illustrated in Flow Diagram V below.

FLOW DIAGRAM V

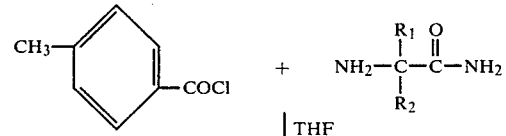

↓ THF

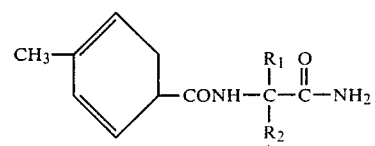

↓ NaOH

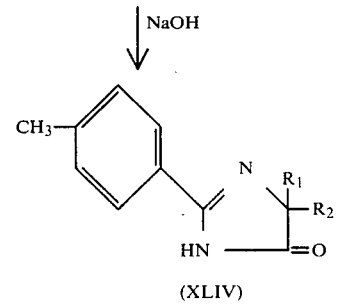

(XLIV)

| 1. Sec BuLi | 1. Sec BuLi |
| 2. $CH_3I$ | 2. $Cl_3C$—$CCl_3$ |

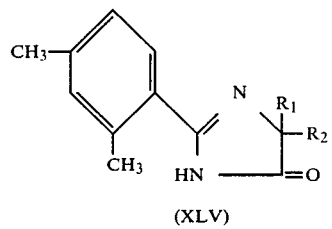

(XLV)

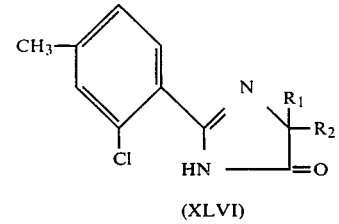

(XLVI)

-continued
FLOW DIAGRAM V

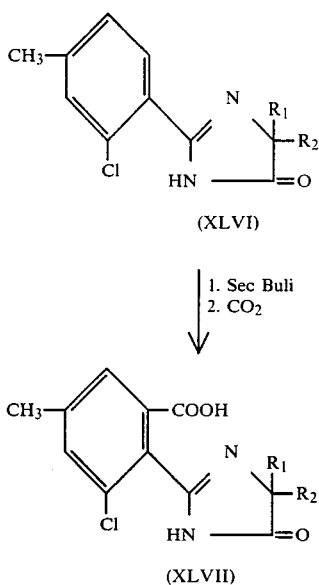

Another alternate route to the preparation of substituted (5-oxo-2-imidazolin-2-yl)benzoic acids, esters and salts is graphically illustrated in Flow Diagram VI below. From this flow sheet, it can be seen that a substituted benzoyl chloride is treated with about 3 to 5 equivalents of a di-$C_1$-$C_3$ alkylamine, such as diethylamine in tetrahydrofuran to yield the corresponding substituted benzamide. This substituted benzamide may then be halogenated, if desired, after treatment thereof with sec-butyl lithium in the presence of tetrahydrofuran or other similar solvent. The sec-butyl lithium is generally dissolved in cyclohexane and added to the benzamide containing reaction mixture while maintaining the temperature thereof below −50° C., e.g. −50° to −75° C. When addition is complete, the mixture is warmed to −30° to −40° C. and a halogenating agent, such as hexachloroethane, dispersed in a non-protic solvent added thereto. This yields the halogenated derivative of the substituted benzamide which is readily converted to the corresponding substituted phthalamic acid by reaction with sec-butyl lithium in tetrahydrofuran and tetramethethylenediamine under a blanket of nitrogen, followed by admixture of the thus-prepared composition with tetrahydrofuran saturated with carbon dioxide. Reaction of the thus-formed substituted phthalamic acid, with ethylchloroformate followed by triethylamine and a solution of a formula XXVI carboxamide in anhydrous tetrahydrofuran, yields the substituted N,N-diethylphthalamides which undergoes base cyclization when heated to 25° to 110° C., with aqueous or aqueous alcoholic sodium or potassium hydroxide. The reaction provides a substituted N,N-dialkyl-(5-oxo-2-imidazolin-2-yl)benzamide which is readily converted to the corresponding acid by treatment with strong mineral acid or to the corresponding ester by transesterification with a $C_1$-$C_3$ alcohol, such as methanol and a strong mineral acid, as shown in Flow Diagram VI. The thus-prepared ester may then be heated with an alkali metal hydroxide and acidified with strong mineral acid to provide the substituted (5-oxo-2-imidazolin-2-yl)benzoic acid. These reactions are illustrated in Flow Diagram VI below, where it can be seen that the final steps of this synthesis route are similar to the latter stages of the preparations illustrated in Flow Diagram IV, although the early stages of the systems differ. It should be noted that when X, Y, Z, and $R_3$ are hydroxyalkyl or $NRH_5$, the group is protected by an acetyl function prior to reactions involving thionyl chloride and during reactions involving acetic anhydride. The acetyl function is removed during or after imidazolinone formation by base. It should also be noted that this reaction sequence results in the formation of an isomer of the compound prepared by Flow Diagram V.

FLOW DIAGRAM VI

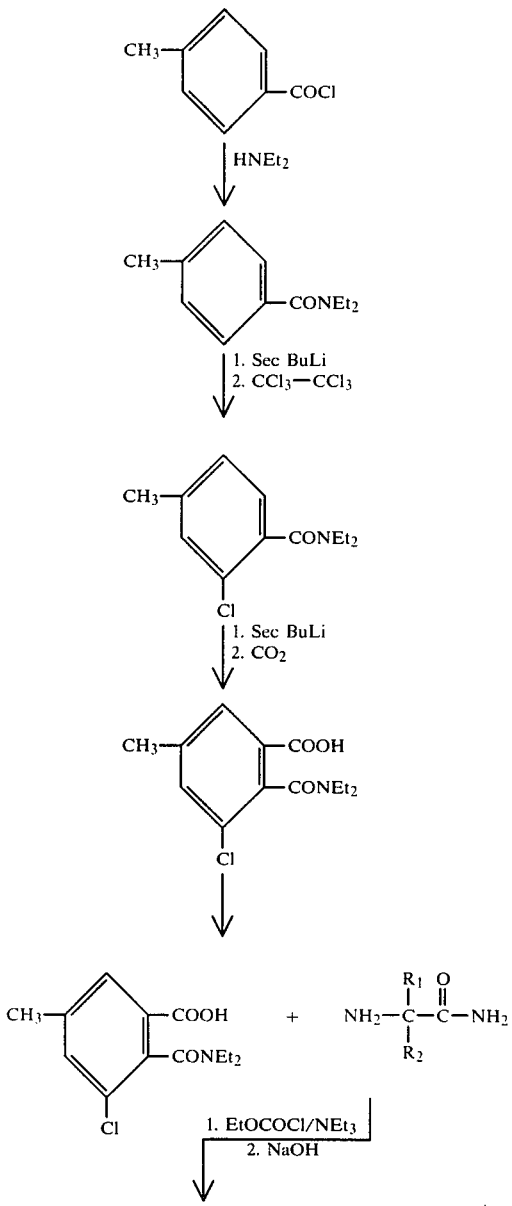

-continued
FLOW DIAGRAM VI

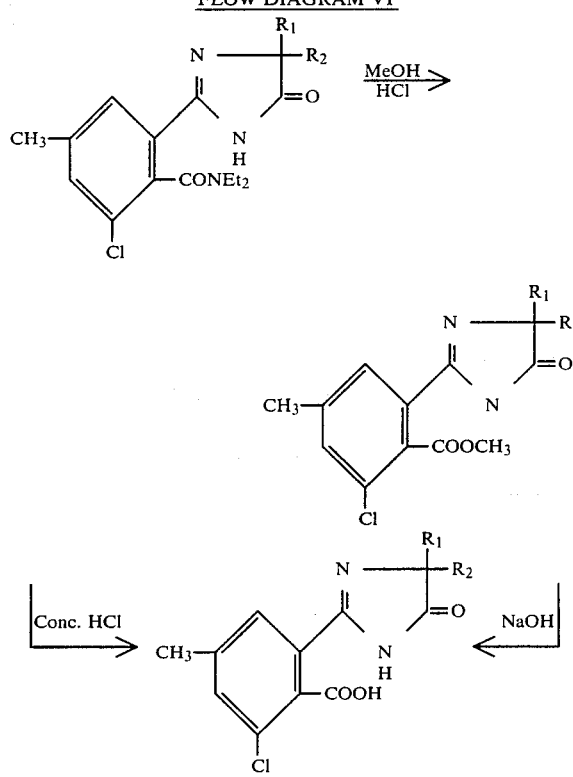

The substituted benzoic acids, esters and salts of this invention are active herbicidal agents effective for controlling a wide variety of annual and perennial plant species including field bindweed, wild oats, quackgrass and, with some compounds, velvetleaf and/or nutsedge. They are also useful as aquatic herbicides and are effective for controlling the above-said plants when applied to the foilage thereof or to soil or water containing seeds or other propagating organs of said plants such as tubers, rhizomes or stolons, at rates of from about 0.125 to 10.0 kg/ha, and preferably at rates from about 0.50 to 4.0 kg/ha.

It is, of course, obvious that rates of application above the 10.0 kg/ha level can also be used to effectively kill undesirable plant species; however, rates of application of toxicant above the level necessary to kill the undesirable plants should be avoided since application of excessive amounts of toxicant is costly and serves no useful function in the environment.

The substituted imidazolinyl benzoic acid, esters and salt of this invention are effective preemergence and postemergence herbicidal agents and some of these are well tolerated by a variety of crops including graminaceous crops and, legumes and sugar beets. They can be applied to the foilage of undesirable plant species or to soil containing seeds or other propagating organs thereof to control the same, and may be used in the form of liquid sprays or solid formulations for such applications.

When the compounds are water soluble they may be simply dissolved in water and applied as such. They may also be formulated as wettable powders, flowable concentrates, emulsifiable concentrates, granular formulations and the like.

Wettable powders can be prepared by grinding together about 20 to 45% by weight of a finely divided carrier such as kaolin, bentonite, diatomaceous earth, attapulgite, or the like, 45 to 80% by weight of the active compound, 2 to 5% by weight of a dispersing agent such as sodium lignosulfonate, and 2 to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5 to 25% by weight of the active ingredient in about 65 to 90% by weight of N-methylpyrrolidone, isophorone, butyl cellosolve, methylacetate or the like and dispersing therein about 5 to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus-prepared solution on a granular carrier such as corncob grits, sand, attapulgite, kaolin or the like.

The granular product thus-prepared generally comprises about 3 to 20% by weight of the active ingredient and about 97 to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 3-chloro-N,N-diethyl-p-toluamide

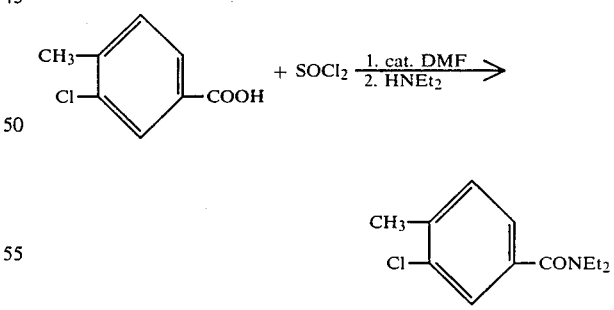

A mixture of 32.2 g (0.19 mol) of 3-chloro-4-methylbenzoic acid in 100 mL of thionyl chloride is treated with 2 drops of dimethylformamide and heated on a steam bath for one hour. The clear amber solution is evaporated in vacuo several times with anhydrous toluene to give a clear amber oily residue. After dilution to a volume of 125 mL with anhydrous tetrahydrofuran, the 3-chloro-4-methyl-benzoyl chloride is added dropwise to a stirred solution of 43.3 mL (0.418 mol) of diethylamine in 300 mL anhydrous tetrahydrofuran under N₂ at −5° C. The reaction mixture is allowed to come to room temperature over a 72 hour period then is treated with 300 mL water. The phases are separated; the aqueous phase is extracted with a total of 300 mL ethyl acetate. All organic phases are combined, washed with 300 ml of a saturated sodium chloride solution, dried over magnesium sulfate and concentrated in vacuo to give 40.0 g of a clear dark red oil. The infrared and proton nmr spectra are consistent with the desired structure. Gas-liquid chromatography analysis gives a purity of 96%.

EXAMPLE 2

Preparation of 3-chloro-4-methylphthalic acid

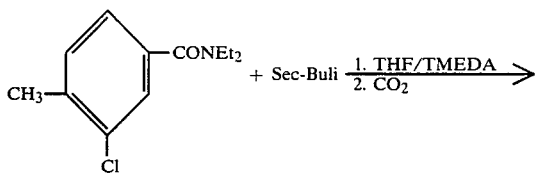

A stirred solution of 16.6 mL (0.11 mol) of N, N, N', N'-tetramethylethylenediamine in 300 mL of anhydrous tetrahydrofuran is treated dropwise with 100 mL of a 1.1 M solution of sec-butyl lithium (0.11 mol) in cyclohexane at −70° to −68° C. under nitrogen. After stirring at −68° C. for 15 minutes, the reaction solution is treated dropwise with a solution of 22.6 g (0.10 mol) of 3-chloro-N,N-diethyl-p-toluamide in 50 mL of anhydrous tetrahydrofuran at −65° to −60° C. The reaction mixture is stirred at −65° C. for 30 minutes, then poured over 350 mL anhydrous THF, saturated with carbon dioxide and allowed to stir at ambient temperatures for four days. The reaction mixture is treated with 300 mL water, the phases are separated, and the aqueous phase is washed with a total volume of 300 mL ethyl acetate. The aqueous phase is cooled to 5° C. and carefully acidified with concentrated sulfuric acid to pH 3. The heavy oil precipitate is extracted into a total of 900 ml of ethyl acetate. These organic phases are combined, washed with 300 mL saturated sodium chloride solution, dried over magnesium sulfate and concentrated to give an orange oily residue (25.1 g) which crystallized on long standing. The infrared and mass spectra are consistent with the desired structure.

EXAMPLE 3

Preparation of 3-chloro-4-methylphthalic anhydride

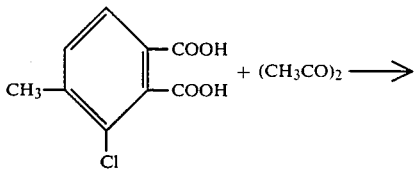

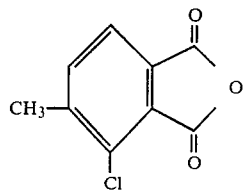

A stirred solution of 21.5 g (0.10 mol) of 3-chloro-4-methylphthalic acid in 300 mL acetic anhydride is heated under reflux for six hours, allowed to cool to room temperature and concentrated in vacuo several times with anhydrous toluene. A viscous, dark, amber syrup is obtained, characterized by an infrared spectrum and used without further purification.

EXAMPLE 4

Preparation of 4-chloro-α-isopropyl-α,5-dimethyl-1,3-dioxo-2-isoindolineacetonitrile

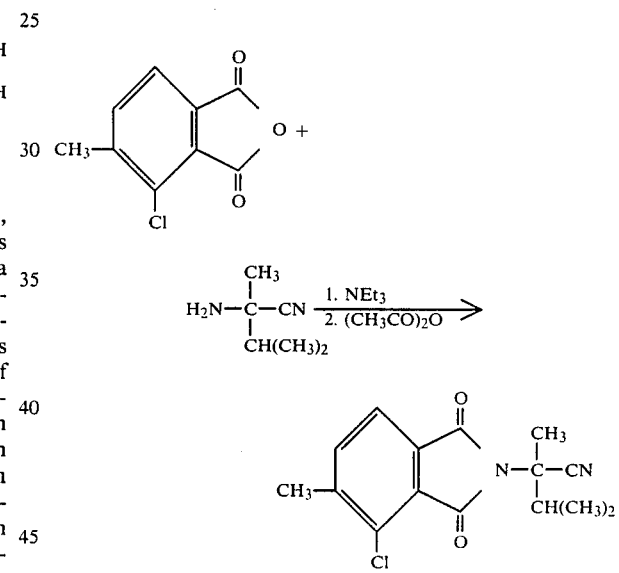

A stirred solution of 19.7 g (0.10 mol) of 3-chloro-4-methylphthalic anhydride in 200 mL anhydrous tetrahydrofuran is treated all at once with a mixture of 12.3 g (0.11 mol) 2-amino-2,3-dimethylbutyronitrile, 13.9 mL (0.10 mol) of triethylamine and 150 mL anhydrous tetrahydrofuran at room temperature. After 72 hours, the solvent is removed in vacuo to give a dark oily residue. This oil is dispersed in 200 mL of acetic anhydride and heated to reflux for two hours, allowed to cool to room temperature over a 48 hour period and concentrated in vacuo to give a heavy black oil. After chromatography on silica gel twice using methylene chloride and mixtures of methylene chloride in hexanes respectively, 14.6 g of a pale yellow solid is obtained, mp 104°–108° C. This solid, 4-chloro-α-isopropyl-α,5-dimethyl-1,3-dioxo-2-isoindolineacetonitrile, is analytically pure and infrared and proton nmr spectra are consistent with desired structure.

EXAMPLE 5

Preparation of
4-chloro-α-isopropyl-α,5-dimethyl-1,3-dioxo-2-isoindolineacetamide

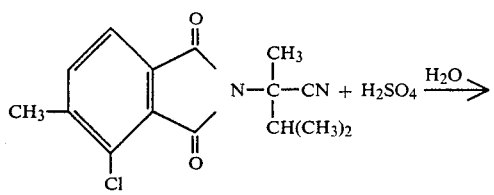

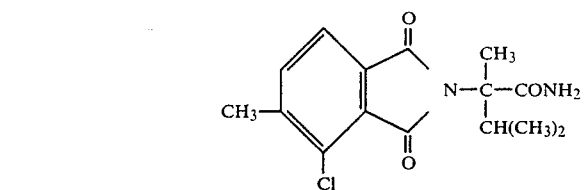

A solution of 9.5 g (0.033 mol) of 4-chloro-α-isopropyl-2,5-dimethyl-1,3-dioxo-2-isoindolineacetonitrile in 30 ml methylene chloride is added dropwise to a mixture of 15 ml 95% sulfuric acid plus 2 mL water at 5° C. Rapid stirring is continued for a total of 24 hours at ambient temperatures. The reaction mixture is heated at 40° C. for three hours and then poured over 250 ml ice. The cold aqueous mixture is extracted with a total volume of 350 ml chloroform. The organic phases are combined, washed with 200 ml water, dried over magnesium sulfate and concentrated in vacuo to give 8.8 g of a light beige solid residue, mp 198°–203° C. This solid can be recrystallized from ethyl acetate/ether to give a analytically pure 4-chloro-α-isopropyl-α,5-dimethyl-1,3-dioxo-2-isoindolineacetamide as a white solid, mp 215°–218° C. The infrared and proton nmr spectra are consistent with the desired structure.

EXAMPLE 6

Preparation of
3-chloro-4-methyl-N-(1-carbamoyl-1,2-dimethylpropyl)-phthalamic acid, methyl ester

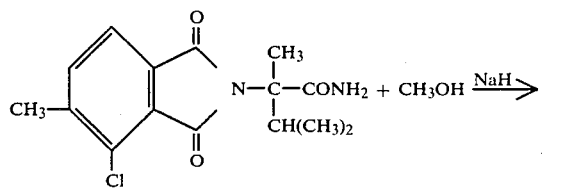

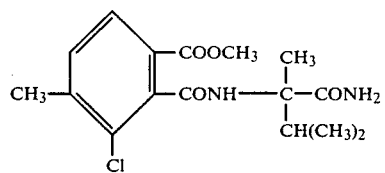

A stirred solution of 6.0 g (0.019 mol) of 4-chloro-2-isopropyl-2,5-dimethyl-1,3-dioxo-2-isoindolinacetamide in 200 ml methanol is treated portion-wise with 0.93 g (0.019 mol) of 50% mineral oil dispersion of sodium hydride. After 16 hours at ambient temperatures, 1.1 ml (0.021 mol) of acetic acid is added dropwise (final pH=7) and the solvents are removed in vacuo. The residue is dispersed in 75 ml water and extracted with a total of 300 ml of ethyl acetate. The organic phases are combined, dried over magnesium sulfate and evaporated in vacuo to give a pale orange gum. After trituration with 50 ml ether and filtration, 4.0 g of a pale orange solid is obtained. The infrared and proton nmr is consistent with the desired structure. This solid is used as is without further purification.

EXAMPLE 7

Preparation of methyl
3-chloro-2-(4-isopropyl-4-methyl-5-oxo-2-imidazolin-2-yl)-p-toluate hydrochloride

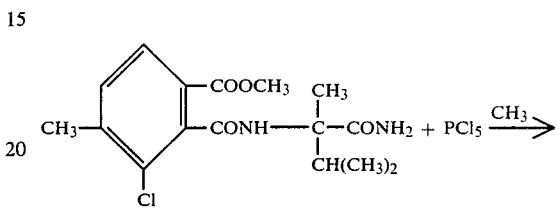

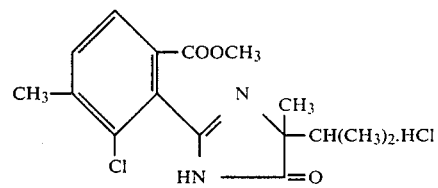

A stirred mixture of 6.1 g (0.029 mol) of phosphorous pentachloride in 100 mL anhydrous toluene is treated portion wise with 4.0 g (0.012 mol) of methyl 3-chloro-4-methyl-N-(1-carbamoyl-1,2-dimethylpropyl)phthalamate. After 72 hours at room temperature, the reaction mixture is poured over 350 ml ice and stirred at ambient temperatures until the ice melts. The resulting three phases are filtered, the off-white solid is dired in vacuo at 53° C. for two hours to give 3.5 g methyl 3-chloro-2-(4-isopropyl-4-methyl-5-oxo-2-(imidazolin-2-yl)-p-toluate hydrochloride, mp 233°–235° C.

EXAMPLE 8

Preparation of methyl
3-chloro-2-(4-isopropyl-4-methyl-5-oxo-2-imidazolin-2-yl)-p-toluate

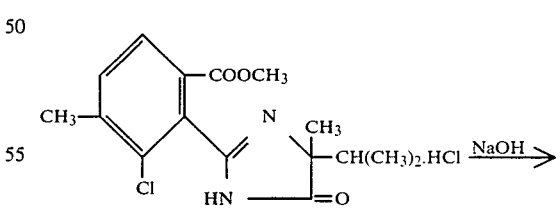

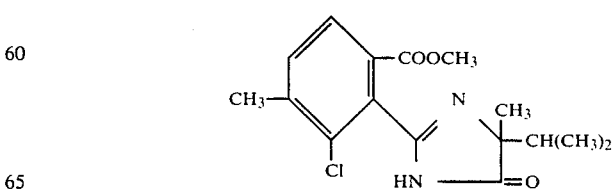

To a dispersion of 1.8 g (5.0 mmol) of the hydrochloride salt prepared in Example 7 in 20 ml water is added 2.5 ml of a 2N sodium hydroxide solution (5.0 mmol) and 50 ml ethyl acetate. With vigorous stirring, the mixture is carefully acidified to pH 3 with concentrated sulfuric acid. The phases are separated and the aqueous phase is extracted with 50 ml ethyl acetate. All organic phases are combined, dried over magnesium sulfate and concentrated in vacuo to give 1.4 g crystalline solid residue, mp 178°–180° C. A sample recrystallized from ethyl acetate gave analytically pure methyl 3-chloro-2-(4-isopropyl-4-methyl-5-oxo-2-imidazolin-2-yl)-p-toluate, mp 181°–183° C.

Example 9

Preparation of 2-methyl 3-nitrophthalate

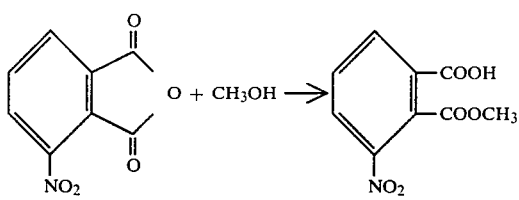

A solution containing 10 g 3-nitrophthalic anhydride in 125 ml absolute ethanol is heated under reflux for 16 hours. Concentration of the solution gives a gray solid residue which is recrystallized from ethyl acetate to give 2-methyl 3-nitrophthalate, mp 154°–156° C.

EXAMPLE 10

Preparation of methyl N-(1-carbamoyl-1,2-dimethylpropyl)-6-nitrophthalamate

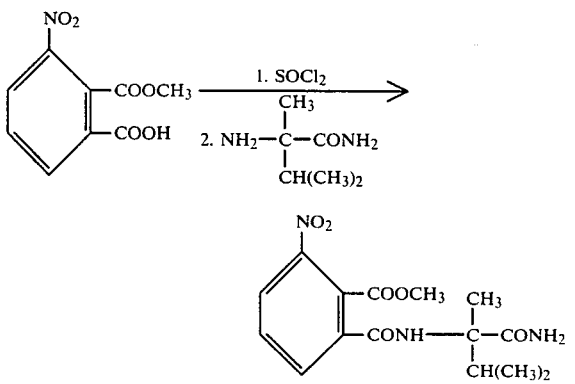

A suspension of 4.94 g 2-methyl-3-nitrophthalate in 20 ml thionyl chloride is stirred at room temperature for 72 hours. The mixture is concentrated and the residue dissolved in toluene and again concentrated. This process is repeated.

The residue (crude acid chloride) in 30 ml dry THF is added dropwise at room temperature with stirring under nitrogen to a solution containing 3.84 g 2-amino-2,3-dimethylbutyramide and 4.4 ml triethylamine in 50 ml dry THF. After stirring at room temperature for 24 hours, 50 ml water and 50 ml CH$_2$Cl$_2$ is added, the phases separated and the aqueous phase reextracted with 50 ml ethyl acetate. The combined organic extract is dried and concentrated. The residue is triturated with ether to give the product which is recrystallized from ethyl acetate to give the desired product with mp 100°–107° C.

EXAMPLE 11

Preparation of methyl 2-(4-isopropyl-4-methyl-5-oxo-2-imidazolin-2-yl)-6-nitrobenzoate

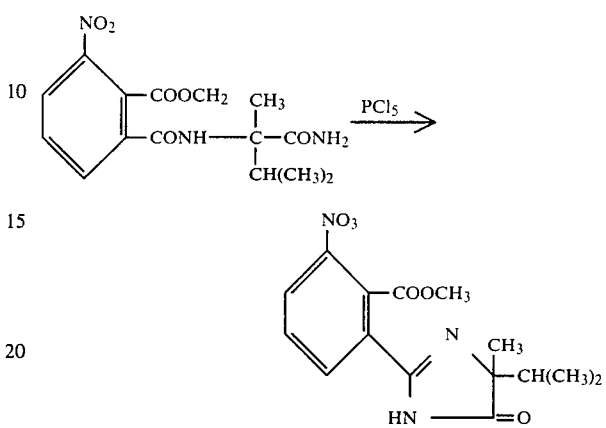

A mixture containing 3.4 g amide and 5.2 g PCl$_5$ in 100 ml dry toluene is heated on a stream bath for one hour. The mixture is cooled to 5° C. and filtered to give 2.6 g hydrochloride salt of the desired imidazolinone, mp 194°–197° C.

This salt is dispersed in a mixture of 20 ml water containing 1.0 g sodium bicarbonate and 75 mL ethyl acetate and the mixture stirred at room temperature for 16 hours. The organic phase is separated, dried and concentrated to give analytically pure methyl 2-(4-isopropyl-4-methyl-5-oxo-2-imidazolin-2-yl)-6-nitrobenzoate, mp 159°–162° C.

EXAMPLE 12

Preparation of 6-fluoro-N,N-diisopropyl-5-methylphthalamic acid

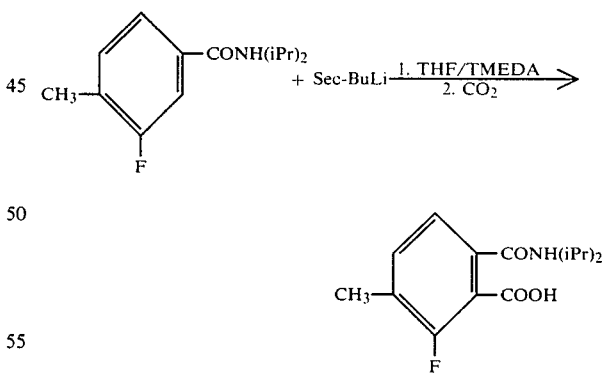

A stirred solution of 7.0 mL (0.046 mol) of N,N,N',N'-tetramethylethylenediamine in 75 mL dry THF under nitrogen is treated dropwise with 42 mL of a 1.1 M solution of sec-BuLi in cyclohexane (0.046 mol) at −75° to −65° C. After addition is complete, a solution of 10.0 g (0.042 mol) of 3-fluoro-N,N-diisopropyl-p-toluamide in 125 ml dry THF is added dropwise at −65° to −60° C. At completion of addition, the reaction mixture is poured over 300 ml of a saturated solution of CO$_2$ in THF and allowed to warm to room temperature. A 125 mL portion of ice water is added (caution, foaming) and the mixture is cautiously acidified to pH 2-3 with concentrated sulfuric acid. The phases are separated, the organic phase is washed with 100 mL of a saturated NaCl solution. The aqueous phases are combined and extracted with a total of 300 mL ethyl acetate. The organic phases are combined, dried over MgSO4 and concentrated in vacuo to give 13.0 g of a yellow glass residue which crystallizes in 200 mL ether to give 8.2 g of 6-fluoro-N,N-diisopropyl-5-methylphthalamic and as an analytically pure white solid, mp 147°-149° C.

EXAMPLE 13

Preparation of N²-(1-carbamoyl-1,2-dimethylpropyl)-3-fluoro-N',N'-diisopropyl-4-methylphthalamide

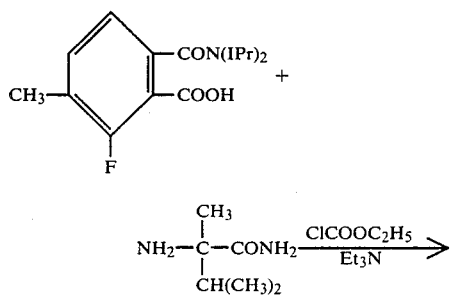

To a stirred solution of 8.18 g 6-fluoro-N,N-diisopropyl-5-methylphthalamic acid in 100 mL dry THF at −2°C. and under nitrogen is added dropwise 2.78 mL ethylchloroformate followed by 4.5 mL triethylamine. After one-half hour, there is added dropwise a solution of 3.77 g 2-amino-2,3-dimethylbutyramide in 125 mL dry THF at −2° to +2° C. After the addition, the mixture is allowed to warm to room temperature and stirred for three hours. To the mixture is added 100 mL water. The organic phase is separated, washed with brine and the combined aqueous phases extracted with 100 mL ethyl acetate. The combined organic phases are dried (MgSO4) and concentrated to give a foam which is used directly in the next step.

EXAMPLE 14

Preparation of 3-fluoro-N,N-diisopropyl-2-(4-isopropyl-4-methyl-5-oxo-2-imidazolin-2-yl)-p-toluamide

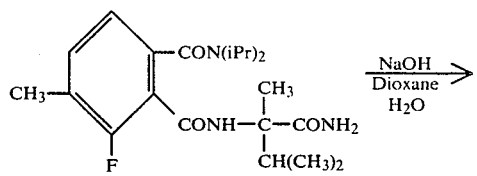

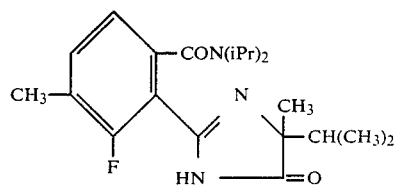

The crude product of Example 13 is dissolved in 75 mL 1.93 N NaOH solution, 25 mL dioxane added and the mixture heated at 80° C. for 16 hours. After cooling, the mixture is acidified with concentrated H2SO4 to pH 3 and extracted several times with ethyl acetate. The extract is washed with brine, dried and concentrated to give a foam which was crystallized from ether to give the product, 3-fluoro-N,N-diisopropyl-2-(4-isopropyl-4-methyl-5-oxo-2-imidazolin-2-yl)-p-toluamide as a white crystalline solid, mp 205°-210° C. which is analytically pure.

EXAMPLE 15

Preparation of 3-fluoro-2-(4-isopropyl-4-methyl-5-oxo-2-imidazolin-2-yl)-p-toluic acid

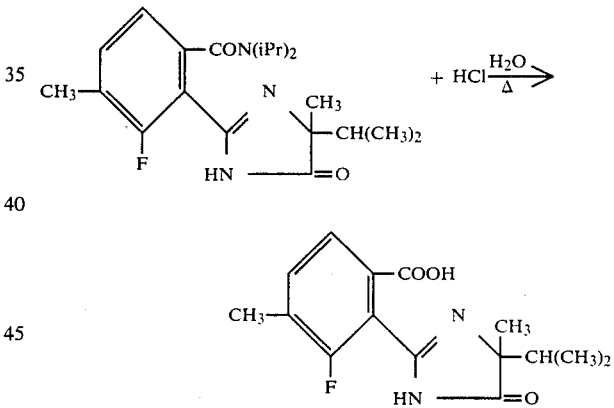

A solution of 1.0 g (2.7 mmols) of 3-fluoro-N,N-diisopropyl-2-(4-isopropyl-4-methyl-5-oxo-2-imidazolin-2-yl)-p-toluamide in 20 mL of concentrated hydrochloric acid is heated to reflux (a copious white solid precipitates). Another 15 mL of concentrated hydrochloric acid is added and the solution is heated under reflux for seven hours. After cooling to room temperature, the mixture is basified to pH 7 to 10 with a 6 N NaOH solution, then carefully adjusted to pH 3 with concentrated sulfuric acid. The mixture is filtered, the clear filtrate is treated with 250 mL ethyl acetate and stirred vigorously for 24 hours. The organic phase is separated, dried over MgSO4 and concentrated in vacuo to give 0.44 g of a white foam which is crystallized ether to give 3-fluoro-2-(4-isopropyl-4-methyl-5-oxo-2-imidazolin-2-yl)-p-toluic acid as a white solid, mp 164°-170° C.

EXAMPLE 16

Preparation of
N-(1-carbamoyl-1,2-dimethylpropyl)-p-toluamide

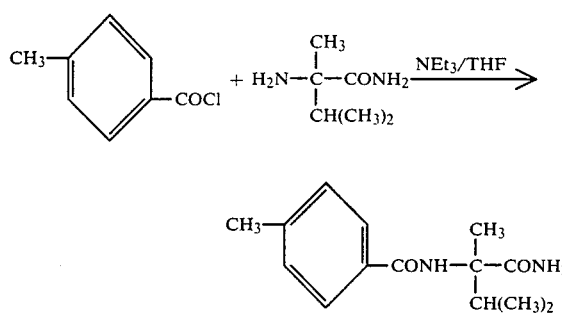

A stirred mmixture containing 13.0 g (0.10 mol) of 2-amino-2,3-dimethylbutyramide and 15.3 mL (0.11 mole) of triethylamine in 150 mL of dry THF is treated dropwise at 5° to 10° C. with a solution of 15.5 g (0.10 mol) of p-toluoyl chloride in 25 mL dry THF. After being allowed to warm to ambient temperatures over a 16 hour period, the reaction mixture is treated with 50 mL water and stirred for one hour. The resulting three phases are filtered; the filtrate is separated and the aqueous phase is extracted with 150 mL ethyl acetate. All organic phases are combined, washed with 100 mL of a saturated NaCl solution, dried over magnesium sulfate and concentrated in vacuo. A white solid residue is obtained which weighs 17.3 g, mp 145°-152° C. The nmr spectrum is consistent with the desired structure.

EXAMPLE 17

Preparation of
4-isopropyl-4-methyl-2-p-tolyl-2-imidazolin-5-one

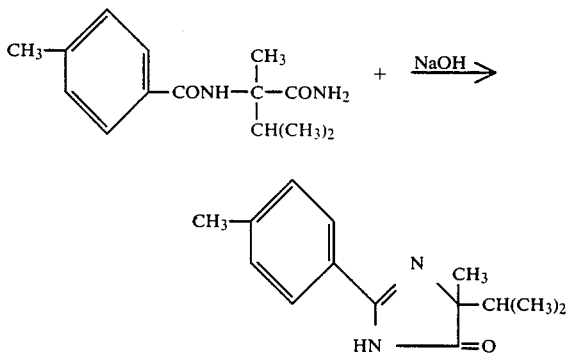

A mixture of 24.8 g (0.10 mol) of N-(1-carbamoyl-1,2-dimethylpropyl)-p-toluamide in 263 mL of a 2N sodium hydroxide solution (0.50 mol NaOH) is heated with 100 mL p-dioxane and heated on a stream bath for 72 hours. The p-dioxane is removed in vacuo and the remaining aqueous solution is cooled to 5°-10° C. After carefully acidifying to pH 3-4 with concentrated sulfuric acid, the reaction mixture is extracted with a total of 750 mL methylene chloride. The organic phase is washed with 200 mL of a saturated sodium chloride solution, dried over magnesium sulfate and evaporated to dryness in vacuo to give a yellow solid residue, weighing 22.1 g. The nmr spectrum is consistent with the desired structure. This compound can be recrystallized from acetonitrile to give analytically pure 4-isopropyl-4-methyl-2-p-tolyl-2-imidazolin-5-one mp 151°-154° C.

EXAMPLE 18

Preparation of
2-(2-chloro-p-tolyl)-4-isopropyl-4-methyl-2-imidazolin-5-one

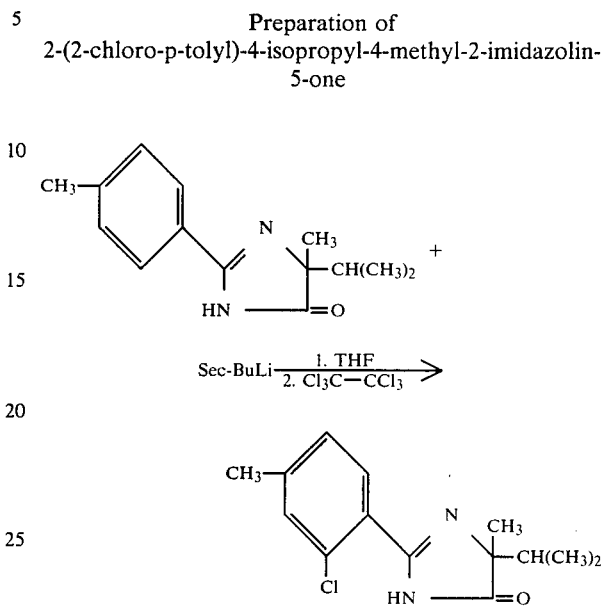

A mechanically stirred solution of 20.0 g (0.087 mol) of 4-isopropyl-4-methyl-2-p-tolyl-2-imidazolin-5-one in 200 mL of dry tetrahydrofuran is treated dropwise with 160 mL of a 1.2 M solution of sec-butyl lithium (0.191 mol) in cyclohexane over a 40 minute period at −72° to −65° C. After stirring the resulting bright red solution at −40° to −35° for one and one-half hours, a solution of 21.4 g (0.090 mol) of hexachloroethane in 125 ml of dry tetrahydrofuran is added dropwise. Addition temperature is allowed to reach −20° C. After warming to room temperature over a 16 hour period, the reaction is treated with 200 mL of ice water plus 200 mL of a saturated sodium chloride solution. The mixture is carefully acidified to pH 3 with concentrated sulfuric acid. The phases are separated and the aqueous phase is extracted with 200 mL ether. The organic phases are combined, dried over magnesium sulfate and concentrated to give a dark brown oily residue. After chromatography on silica gel using mixtures of ether in methylene chloride as eluent, the product (6.7) g is obtained as a light beige solid, mp 156°-160° C. The infrared and proton nmr spectra are consistent with the desired structure. A sample recrystallized from ether had mp 152°-165° C. and was analytically pure.

EXAMPLE 19

Preparation of
5-chloro-6-(4-isopropyl-4-methyl-5-oxo-2-imidazolin-2-yl)-m-toluic acid

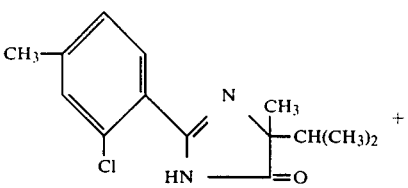

-continued

Sec-BuLi $\xrightarrow[\text{2. CO}_2]{\text{1. THF/TMEDA}}$

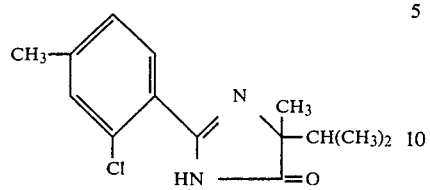

A stirred solution of 3.7 g (0.014 mol) of 2-(2-chloro-p-tolyl)-4-isopropyl-4-methyl-2-imidazolin-5-one in 70 mL anhydrous tetrahydrofuran and 4.7 mL (0.031 mol) of N,N,N',N'-tetramethylethylenediamine under $N_2$ is treated at $-70°$ to $-63°$ C. dropwise with 26 ml of a 1.2 M solution of sec-butyl lithium (0.031 mol) in cyclohexane. After stirring for two hours at $-55°$ to $-45°$ C., the reaction is poured over 300 mL anhydrous THFsaturated with carbon dioxide. The mixture is allowed to come to room temperature over a 16 hour period and then treated with 250 mL water and carefully acidified with ice cooling, to pH 3 with concentrated sulfuric acid. The phases are separated; the aqueous phase is extracted with 150 mL of ethyl acetate. The organic phases are combined and extracted with 50 mL of an 0.5 N solution of sodium hydroxide. The basic aqueous phase is cooled to 5°-10° C. and carefully acidified to pH 3 with concentrated sulfuric acid to give a fine white solid precipitate. After filtration, the solid is dried in vacuo at 54° C. for 16 hours to give 3.5 g product, mp 240°-245° C. An analytically pure sample of 5-chloro-6-(4-isopropyl-4-methyl-5-oxo-2-imidazolin-2-yl)-m-toluic acid, mp 245°-248° C., is obtained by recrystallization of the product from ethanol.

EXAMPLE 20

Preparation of 2-(5-imidazolidinyl)benzoic acids and esters

The procedures described in Examples 9–11, 12–15 and 16–19 are effective for preparing a wide variety of substituted and unsubstituted 2-(2-imidazolin-2-yl)benzoic acids and esters. Among the 2-(2-imidazolin-2-yl)benzoic acids and esters prepared by these procedures are those described below in Table I.

TABLE I

Compounds prepared by the procedures described in Examples 1–19 having the structure:

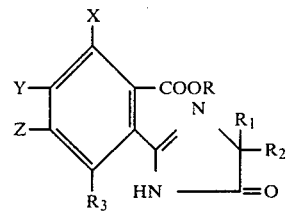

| R | $R_1$ | $R_2$ | X | Y | Z | $R_3$ | mp °C. |
|---|---|---|---|---|---|---|---|
| $CH_3$ | $CH_3$ | $CH(CH_3)_2$ | H | $CF_3$ | $(CF_3)$ | H | 109–121 |
| H | $CH_3$ | $CH(CH_3)_2$ | H | $CF_3$ | H | H | 214.5–216 |
| $CH_3$ | $CH_3$ | $CH(CH_3)_2$ | H | OH | (OH) | H | 119–129 |
| $CH_3$ | $CH_3$ | $CH(CH_3)_2$ | H | H | H | $NH_2$ | 142–150 |
| H | $CH_3$ | $CH(CH_3)_2$ | H | H | H | $N(CH_3)_2$ | 210–217 |
| $CH_3$ | $CH_3$ | $CH(CH_3)_2$ | H | H | H | $N(CH_3)_2$ | 125–133 |
| $CH_3$ | $CH_3$ | $CH(CH_3)_2$ | H | $OCH_3$ | H | H | 54–60 |
| H | $CH_3$ | $CH(CH_3)_2$ | H | $OCH_3$ | H | H | 188.5–190 |
| $CH_3$ | $CH_3$ | $CH(CH_3)_2$ | $OCH_3$ | H | H | H | 145–148 |
| H | $CH_3$ | $CH(CH_3)_2$ | $OCH_3$ | H | H | H | 188–190 |
| $CH_3$ | $CH_3$ | $CH(CH_3)_2$ | H | H | H | $OCH_3$ | 158–163 |
| H | $Ch_3$ | $CH(CH_3)_2$ | H | H | H | $CF_3$ | 213–215 |
| H | $CH_3$ | $CH(CH_3)_2$ | H | H | H | $OCH_3$ | 196–200 ½ $H_2SO_4$ salt |
| $CH_3$ | $CH_3$ | $CH(CH_3)_2$ | H | H | H | $CF_3$ | 161–165 |
| $CH_2C_6H_5$ | $CH_3$ | $CH(CH_3)_2$ | H | $CH_3$ | $CH_3$ | H | 149–152 |
| $CH_2\text{-furyl}$ | $CH_3$ | $CH(CH_3)_2$ | H | $CH_3$ | $CH_3$ | H | 129–137 |
| $^+NH_3-CH(CH_3)_2$ | $CH_3$ | $CH(CH_3)_2$ | H | $CH_3$ | $CH_3$ | H | glass |
| $CH_3$ | $CH_3$ | $CH(CH_3)_2$ | H | $CH_3$ | $CH_3$ | H | 140–141 |
| $CH_2C\equiv CH$ | $CH_3$ | $CH(CH_3)_2$ | H | $CH_3$ | $CH_3$ | H | 165–167 |
| H | $CH_3$ | $CH(CH_3)_2$ | H | $CH_3$ | $CH_3$ | H | 188–189 |
| H | $CH_3$ | $CH(CH_3)_2$ | H | $CH_3$ | $CH_3$ | H | 259–263 (dec) (HCl salt) |
| $CH_3$ | $CH_3$ | $CH(CH_3)_2$ | H | $CH_3$ | H | $CH_3$ | 167–169.5 |
| H | $CH_3$ | $CH(CH_3)_2$ | H | $CH_3$ | H | $CH_3$ | 206–208.5 |
| $CH_3$ | $CH_3$ | $CH(CH_3)_2$ | H | H | $CH_3$ | $CH_3$ | 173.5–177 |
| H | $CH_3$ | $CH(CH_3)_2$ | H | H | $CH_3$ | $CH_3$ | 177–198 |
| H | $CH_3$ | $CH(CH_3)_2$ | H | Cl | $CH_3$ | H | 188–191 |
| $CH_3$ | $CH_3$ | $CH(CH_3)_2$ | H | Cl | $CH_3$ | H | 118–132 |
| H | $CH_3$ | $CH(CH_3)_2$ | Cl | $CH_3$ | H | H | 213–222 |
| $CH_3$ | $CH_3$ | $CH(CH_3)_2$ | F | $CH_3$ | H | H | 129–132 |
| $CH_3$ | $CH_3$ | $CH(CH_3)_2$ | H | $-(CH_2)_4-$ | | H | 145–152 |

TABLE I-continued

Compounds prepared by the procedures described in Examples 1-19 having the structure:

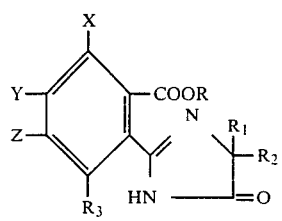

| R | $R_1$ | $R_2$ | X | Y | Z | $R_3$ | mp °C. |
|---|---|---|---|---|---|---|---|
| H | $CH_3$ | $CH(CH_3)_2$ | H | —(CH$_2$)$_4$— | | H | 200–203 |
| H | $CH_3$ | $CH(CH_3)_2$ | H | $CH_3$ | H | Cl | 245–248 |
| $CH_3$ | $CH_3$ | $CH(CH_3)_2$ | H | $CH_3$ | H | Cl | 184–189 |
| H | $CH_3$ | $CH(CH_3)_2$ | $CH_3$ | H | $CH_3$ | H | 200–207 |
| $CH_2C\equiv CH$ | $CH_3$ | $CH(CH_3)_2$ | $CH_3$ | H | $CH_3$ | H | 121–125 |
| $CH_3$ | $CH_3$ | $CH(CH_3)_2$ | $CH_3$ | H | $CH_3$ | H | 145–148 |
| $CH_3$ | $CH_3$ | $CH(CH_3)_2$ | H | Cl | Cl | H | 170–173 |
| H | $CH_3$ | $CH(CH_3)_2$ | H | Cl | Cl | H | 223–224 |
| $CH_3$ | $CH_3$ | $CH(CH_3)_2$ | H | H | $CH_3$ | Cl | 181–183 |
| $CH_3$ | $CH_3$ | $CH(CH_3)_2$ | $CH_3$ | H | H | $CH_3$ | 124–146 |
| H | $CH_3$ | $CH(CH_3)_2$ | $CH_3$ | —CH=CH—CH=CH— | | H | >250 HCl salt |
| H | $CH_3$ | $CH(CH_3)_2$ | $CH_3$ | H | $CH_3$ | Cl | 196–204 |
| H | $CH_3$ | $CH(CH_3)_2$ | $CH_3$ | H | H | $CH_3$ | 225.5–229 |
| H | $CH_3$ | $CH(CH_3)_2$ | H | H | $CH_3$ | F | 164–170 |
| $CH_3$ | $CH_3$ | $CH(CH_3)_2$ | H | H | $CH_3$ | F | 145–153 |
| $CH_3$ | $CH_3$ | $CH(CH_3)_2$ | H | H | $CH_2OH$ | H | 195–199 |
| $CH_3$ | $CH_3$ | $CH(CH_3)_2$ | H | —(CH$_2$)$_3$— | | H | 142–144 |
| $CH_3$ | $CH_3$ | $CH(CH_3)_2$ | —(CH$_2$)$_3$— | H | | H | 139–142 |
| H | $CH_3$ | $CH(CH_3)_2$ | H | —(CH$_2$)$_3$— | | H | 186–189 |
| H | $CH_3$ | $CH(CH_3)_2$ | —(CH$_2$)$_3$— | H | | H | 157–161 |
| H | $CH_3$ | $CH(CH_3)_2$ | H | H | $CH_2OH$ | H | 214–218 |
| $CH_3$ | $CH_3$ | $CH(CH_3)_2$ | H | $CH_2OH$ | H | H | 229–231 |
| H | $CH_3$ | $CH(CH_3)_2$ | H | $CH_2OH$ | H | H | 207–210 |
| H | $CH_3$ | $CH(CH_3)_2$ | H | —(CH$_2$)$_2$— | | H | 201–203 |
| $CH_3$ | $CH_3$ | $CH(CH_3)_2$ | H | —(CH$_2$)$_2$— | | H | 130–135 |
| $CH_3$ | $CH_3$ | $CH(CH_3)_2$ | H | H | | $SCH_3$ | 113–115 |
| $CH_3$ | $CH_3$ | $CH(CH_3)_2$ | H | $CH_2F$ | H | H | 113–118 |
| H | $CH_3$ | $CH(CH_3)_2$ | H | H | H | $SCH_3$ | 201–204 |
| $CH_3$ | $CH_3$ | $CH(CH_3)_2$ | H | $SCH_3$ | H | H | 130–131 |
| H | $CH_3$ | $CH(CH_3)_2$ | H | $SCH_3$ | H | H | 105–116 |
| H | $CH_3$ | $CH(CH_3)_2$ | H | $CH_2F$ | H | H | 205–210 |
| $CH_3$ | $CH_3$ | $CH(CH_3)_2$ | H | $OCHF_2$ | $(OCHF_2)$ | H | 155–157 IM |
| $CH_3$ | $CH_3$ | $CH(CH_3)_2$ | $OCHF_2$ | H | H | $(OCHF_2)$ | 119–129 IM |
| H | $CH_3$ | $CH(CH_3)_2$ | H | $OCHF_2$ | $(OCHF_2)$ | H | 146–148 IM |
| $CH_3$ | $CH_3$ | $CH(CH_3)_2$ | H | H | $CH_2F$ | H | 117–119 |
| $CH_3$ | $CH_3$ | $CH(CH_3)_2$ | H | $OCF_3$ | H | H | 99–102 |
| H | $CH_3$ | $CH(CH_3)_2$ | H | $OCF_3$ | H | H | 250–251 |

IM = isomeric mixture where second on the ring is shown in ( ).

EXAMPLE 21

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ® 20, a polyoxyethylene sorbitan monolaurate surfactant of Atlas Chemical Industries, in sufficient quantities to provide the equivalent of about 0.125 kg to 10.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table II below.

| Rating System | % Difference in Growth from the Check |
|---|---|
| 0 - No Effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | | Plant Species Used | |
|---|---|---|---|
| Barnyardgrass | (Echinochloa crusgalli) | Velvetleaf | (Abutilon theophrasti) |
| Purple Nutsedge | (Cyperus rotundus L.) | Barley | (Hordeum vulgare) |
| Wild Oats | (Avena fatua) | Corn | (Zea mays) |
| Quackgrass | (Agropyron repens) | Soybean | (Glycine max) |
| Field Bindweed | (Convolvulus arvensis L.) | Wheat | (Triticum aestivum) |
| Morningglory | (Ipomoea purpurea) | | |

TABLE II

POST-EMERGENCE TESTS - RATES IN KG/HA

| Compound | RATE | BARN-YARD GR | P NUT SEDGE | WILD OATS | QUACK GRASS | FLD B INDWD | MRN-GLRY SP | VEL-VET LEAF | 5 BAR LY LA | CORN FIELD | SOY-BEAN WI |
|---|---|---|---|---|---|---|---|---|---|---|---|
| Methyl α,α,α-trifluoro-6-(4-isopropyl-4-methyl-5-oxo-2-imidazolin-2-yl)-m-toluate and methyl α,α,α,-trifluoro-2-(4-isopropyl-4-methyl-5-oxo-2-imidazolin-2-yl)-p-toluate; | 2.000 | 9.0 | | 7.0 | 0.0 | | | 3.0 | 0.0 | 2.0 | |
| | 1.000 | 8.0 | | 3.0 | 0.0 | | | 2.0 | 0.0 | 0.0 | |
| α,α,α-trifluoro-6-(4-isopropyl-4-methyl-5-oxo-2-imidazolin-2-yl)-m-toluic acid; | 8.000 | 6.0 | 0.0 | 9.0 | 0.0 | 0.0 | 5.0 | 1.0 | | | |
| | 2.000 | 0.0 | 0.0 | 3.5 | 0.0 | 8.0 | 6.0 | 3.0 | 0.0 | 0.0 | 0.0 |
| | 1.000 | 0.0 | 0.0 | 1.5 | 0.0 | 9.0 | 4.0 | 1.5 | 0.0 | 0.0 | 0.0 |
| | .500 | 0.0 | 0.0 | 0.0 | 0.0 | 8.0 | 2.0 | 0.5 | 0.0 | 0.0 | 0.0 |
| | .250 | 0.0 | 0.0 | 0.0 | 0.0 | 7.0 | 2.0 | 0.0 | 0.0 | 0.0 | 0.0 |
| 3-(dimethylamino)-2-(4-isopropyl-4-methyl-5-oxo-2-imidazolin-2-yl)-benzoic acid; | 8.000 | 9.0 | 2.0 | 9.0 | 0.0 | 1.0 | 5.0 | 1.0 | | | |
| | 2.000 | 0.0 | 0.0 | 0.0 | 2.0 | 3.0 | 0.0 | 3.0 | 6.0 | 0.0 | 0.0 |
| Methyl 3-amino-2-(4-isopropyl-4-methyl-5-oxo-2-imidazolin-2-yl)-benzoate; | 8.000 | | 1.0 | | 0.0 | 3.0 | | | | | |
| | 2.000 | 3.0 | 0.0 | 3.0 | 0.0 | 3.0 | 0.0 | 3.0 | 0.0 | 9.0 | 3.0 |
| | 1.000 | 0.0 | 0.0 | 0.0 | 0.0 | 1.0 | 0.0 | 0.0 | 0.0 | 9.0 | 2.0 |
| | .500 | 0.0 | 0.0 | 0.0 | 0.0 | 0.0 | 0.0 | 0.0 | 0.0 | 9.0 | 0.0 |
| | .250 | 0.0 | 0.0 | 0.0 | 0.0 | 0.0 | 0.0 | 0.0 | 0.0 | 9.0 | 0.0 |
| | .125 | 0.0 | 0.0 | 0.0 | 0.0 | 0.0 | 0.0 | 0.0 | 0.0 | 2.0 | 0.0 |
| | .063 | 0.0 | 0.0 | 0.0 | 0.0 | 0.0 | 0.0 | 0.0 | 0.0 | 1.0 | 0.0 |
| Methyl 2-(4-isopropyl-4-methyl-5-oxo-2-imidazolin-2-imidazolin-2-yl)-4,5-dimethylbenzoate; | 10.000 | 0.0 | 0.0 | 9.0 | | | 0.0 | 3.0 | | | |
| | 2.000 | 0.0 | 0.0 | 9.0 | | | 0.0 | 0.0 | | 3.0 | 0.0 |
| | 1.000 | 0.0 | 0.0 | 9.0 | | | 0.0 | 0.0 | | 1.0 | 0.0 |
| | .500 | 0.0 | 0.0 | 6.0 | | | 0.0 | 0.0 | | 0.0 | 0.0 |
| 2-Propynyl 2(4-isopropyl-4-methyl-5-oxo-2-imidazolin-2-yl)-4,5-dimethylbenzoate; | 10.000 | | 1.0 | 9.0 | | | 3.0 | | | | |
| | 2.000 | 2.5 | 2.0 | 9.0 | 0.0 | 9.0 | 1.0 | 2.0 | 9.0 | 7.5 | 1.5 |
| | 1.000 | 1.0 | 1.0 | 9.0 | 0.0 | 7.0 | 0.0 | 1.5 | 9.0 | 7.5 | 1.5 |
| | .500 | 0.5 | 0.0 | 8.0 | 0.0 | | 0.0 | 0.5 | 3.0 | 6.0 | 0.0 |
| | .250 | 0.0 | 0.0 | 4.0 | 0.0 | 3.0 | 0.0 | 0.0 | 2.0 | 1.0 | 0.0 |
| Ethyl 2-(4-isopropyl-4-methyl-5-oxo-2-imidazolin-2-yl)-4,5-dimethylbenzoate; | 10.000 | 0.0 | 0.0 | 9.0 | | | 0.0 | 0.0 | | | |
| 2-(4-Isopropyl-4-methyl-5-oxo-2-imidazolin-2-yl)-4,5-dimethylbenzoic acid; | 10.000 | 7.0 | 5.0 | 9.0 | | | 3.0 | 9.0 | | | |
| | 2.000 | 5.0 | 0.0 | 9.0 | | | 0.0 | 5.0 | | 8.0 | 1.0 |
| | 1.000 | 0.0 | 0.0 | 7.0 | | | 0.0 | 0.0 | | 7.0 | 0.0 |
| | .500 | 0.0 | 0.0 | 3.0 | | | 0.0 | 0.0 | | 5.0 | 0.0 |
| 2-(4-isopropyl-4-methyl-5-oxo-2-imidazolin-2-yl)-4,5-dimethylbenzoic acid hydrochloride; | 10.000 | 7.0 | 7.0 | 9.0 | | | 5.0 | 9.0 | | | |
| | 2.000 | 5.0 | 0.0 | 9.0 | | | 0.0 | 3.0 | | 8.0 | 3.0 |
| | 1.000 | 0.0 | 0.0 | 8.0 | | | 0.0 | 0.0 | | 7.0 | 3.0 |
| | .500 | 0.0 | 0.0 | 7.0 | | | 0.0 | 0.0 | | 5.0 | 0.0 |
| | .250 | 0.0 | 0.0 | 5.0 | | | 0.0 | 0.0 | | 3.0 | 0.0 |
| 5-Chloro-6-(5-isopropyl-5-methyl-4-oxo-2-imidazolin-2-yl)-m-toluic acid; | 2.000 | 9.0 | 0.0 | 9.0 | 0.0 | 7.0 | 8.0 | 5.0 | 0.0 | 0.0 | 3.0 |
| | 1.000 | 0.0 | 0.0 | 7.0 | 0.0 | 7.0 | 5.0 | 3.0 | 0.0 | 0.0 | 0.0 |
| | .500 | 0.0 | 0.0 | 4.0 | 0.0 | 7.0 | 0.0 | 1.0 | 0.0 | 0.0 | 0.0 |
| | .250 | 0.0 | 0.0 | 0.0 | 0.0 | 4.0 | 0.0 | 0.0 | 0.0 | 0.0 | 0.0 |
| 2-(4-Isopropyl-4-methyl-5-oxo-2-imidazolin-2-yl)-3,5-dimethylbenzoic acid; | 2.000 | 7.0 | 7.0 | 9.0 | 6.0 | 8.0 | 8.0 | 9.0 | 8.0 | 5.0 | 6.0 |
| | 1.000 | 6.0 | 5.0 | 9.0 | 4.0 | 8.0 | 8.0 | 8.0 | 8.0 | 5.0 | 6.0 |
| | .500 | 6.0 | 2.0 | 8.0 | 4.0 | 9.0 | 8.0 | 7.0 | 5.0 | 5.0 | 6.0 |
| | .250 | 3.0 | 0.0 | 7.0 | 0.0 | 9.0 | 8.0 | 7.0 | 6.0 | 2.0 | 4.0 |
| | .125 | 2.0 | 0.0 | 7.0 | 0.0 | 9.0 | 8.0 | 4.0 | 3.0 | 2.0 | 3.0 |
| | .063 | 1.0 | 0.0 | 2.0 | 0.0 | 8.0 | 6.0 | 3.0 | 2.0 | 1.0 | 2.0 |
| 2-(4-Isopropyl-4-methyl-5-oxo-2-imidazolin-2-yl)-3,4-dimethylbenzoic acid; | 2.000 | 6.0 | 0.0 | 6.0 | 0.0 | 8.0 | 8.0 | 5.0 | 0.0 | 6.0 | 3.0 |
| | 1.000 | 5.0 | 0.0 | 4.0 | 0.0 | 9.0 | 8.0 | 6.0 | 0.0 | 6.0 | 2.0 |
| | .500 | 2.0 | 0.0 | 3.0 | 0.0 | 9.0 | 8.0 | 6.0 | 0.0 | 6.0 | 2.0 |
| | .250 | 0.0 | 0.0 | 1.0 | 0.0 | 0.0 | 7.0 | 3.0 | 0.0 | 5.0 | 1.0 |
| | .125 | 0.0 | 0.0 | 0.0 | 0.0 | 0.0 | 8.0 | 1.0 | 0.0 | 4.0 | 1.0 |
| | .063 | 0.0 | 0.0 | 0.0 | 0.0 | 0.0 | 6.0 | 0.0 | 0.0 | 4.0 | 0.0 |
| 2-(4-Isopropyl-4-methyl-5-oxo-2-imidazolin-2-yl)-4,6-dimethylbenzoic acid; | 2.000 | 5.0 | 6.0 | 0.0 | 0.0 | 9.0 | 6.0 | 6.0 | 0.0 | 2.0 | 6.0 |
| | 1.000 | 3.0 | 5.0 | 0.0 | 0.0 | 8.0 | 6.0 | 4.0 | 0.0 | 1.0 | 5.0 |
| | .500 | 2.0 | 4.0 | 0.0 | 0.0 | 6.0 | 4.0 | 3.0 | 0.0 | 0.0 | 5.0 |
| | .250 | 0.0 | 3.0 | 0.0 | 0.0 | 2.0 | 4.0 | 3.0 | 0.0 | 0.0 | 4.0 |
| 6-(4-isopropyl-4-methyl-5-oxo-2-imidazolin-2-yl)-m-anisic acid; | 2.000 | 8.0 | 7.0 | 7.0 | 8.0 | 9.0 | 6.0 | 6.0 | 6.0 | 4.0 | 7.0 |
| | 1.000 | 6.0 | 4.0 | 4.0 | 4.0 | 7.0 | 4.0 | 4.0 | 4.0 | 3.0 | 4.0 |
| | .500 | 4.0 | 3.0 | 3.0 | 0.0 | 6.0 | 3.0 | 1.0 | 4.0 | 6.0 | 3.0 |

TABLE II-continued

POST-EMERGENCE TESTS - RATES IN KG/HA

| Compound | RATE | BARN-YARD GR | P NUT SEDGE | WILD OATS | QUACK GRASS | FLD B INDWD | MRN-GLRY SP | VEL-VET LEAF | 5 BAR LY LA | CORN FIELD | SOY-BEAN WI |
|---|---|---|---|---|---|---|---|---|---|---|---|
| | .250 | 3.0 | 0.0 | 2.0 | 0.0 | 3.0 | 0.0 | 0.0 | 2.0 | 3.0 | 3.0 |
| | .125 | 0.0 | 0.0 | 1.0 | 0.0 | 0.0 | 0.0 | 0.0 | 2.0 | 2.0 | 2.0 |
| Furfuryl 2-(4-isopropyl-4- | 2.000 | 9.0 | 0.0 | 8.0 | 4.0 | 0.0 | 0.0 | 9.0 | 4.0 | 3.0 | 5.0 |
| methyl-5-oxo-2-imidazolin- | 1.000 | 7.0 | 0.0 | 3.0 | 0.0 | 0.0 | 0.0 | 0.0 | 3.0 | 3.0 | 4.0 |
| 2-yl)-4,5-dimethylbenzoate; | .500 | 4.0 | 0.0 | 2.0 | 0.0 | 0.0 | 0.0 | 0.0 | 2.0 | 1.0 | 2.0 |
| | .250 | 2.0 | 0.0 | 0.0 | 0.0 | 0.0 | 0.0 | 0.0 | 2.0 | 1.0 | |
| | .125 | 0.0 | 0.0 | 0.0 | 0.0 | 0.0 | 0.0 | 0.0 | 2.0 | 0.0 | 2.0 |
| Isopropylammonium 2-(4- | 2.000 | 9.0 | 0.0 | 9.0 | 7.0 | 8.0 | 3.0 | 6.0 | 9.0 | 6.0 | 3.0 |
| isopropyl-4-methyl-5-oxo- | 1.000 | 5.0 | 0.0 | 9.0 | 3.0 | 5.0 | 2.0 | 2.0 | 7.0 | 5.0 | 3.0 |
| 2-imidazolin-2-yl)-4,5- | .500 | 3.0 | 0.0 | 9.0 | 2.0 | 3.0 | 1.0 | 1.0 | 7.0 | 2.0 | 3.0 |
| dimethylbenzoic acid; | .250 | 0.0 | 0.0 | 6.0 | 1.0 | 1.0 | 0.0 | 0.0 | 7.0 | 3.0 | 2.0 |
| | .125 | 0.0 | 0.0 | 1.0 | 0.0 | 0.0 | 0.0 | 0.0 | 3.0 | 0.0 | 0.0 |

EXAMPLE 22

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.063 to 10.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table III below. Where more than one test is involved for a given compound, the data are averaged.

TABLE III

PRE-EMERGENCE TESTS - RATES IN KG/HA

| Compound | RATE | BARNY ARDGR | P NUT SEDGE | WILD OATS | QUACK GRASS | FLD B INDWD | MRNGL RY SP | VELVE TLEAF | S BAR LY LA | CORN FIELD | SOYBE AN WI | WHE AT ER |
|---|---|---|---|---|---|---|---|---|---|---|---|---|
| Methyl α,α,α-trifluoro-6-(4-isopropyl-4-methyl-5-oxo-2-imidazolin-2-yl)-m-toluate and methyl α,α,α-trifluoro-2-(4-isopropyl-4-methyl-5-oxo-2-imidazolin-2-yl)-p-toluate; | 2.000 | 5.0 | | 8.0 | 9.0 | 9.0 | | 8.0 | 7.0 | 9.0 | | |
| | 1.000 | 4.0 | | 6.0 | 9.0 | 9.0 | | 6.0 | 2.0 | 2.0 | | |
| | .500 | 0.0 | | 5.0 | 0.0 | 0.0 | | 2.0 | 0.0 | 0.0 | | |
| | .250 | 0.0 | | 2.0 | 0.0 | 0.0 | | 0.0 | 0.0 | 0.0 | | |
| α,α,α-trifluoro-6-(4-isopropyl-4-methyl-5-oxo-2-imidazolin-2-yl)-m-toluic acid; | 8.000 | 9.0 | 9.0 | 8.0 | 9.0 | 9.0 | 5.0 | 6.0 | 0.0 | 0.0 | 0.0 | |
| | 2.000 | 0.0 | 0.0 | 4.0 | 9.0 | 9.0 | 5.0 | 3.0 | 0.0 | 0.0 | 0.0 | |
| | 1.000 | 0.0 | 0.0 | 3.0 | 0.0 | 0.0 | 3.0 | 0.0 | 0.0 | 0.0 | 0.0 | |
| | .500 | 0.0 | 0.0 | 2.0 | 2.0 | 0.0 | 0.0 | 0.0 | 0.0 | 0.0 | 0.0 | |
| 3-(dimethylamino)-2-(4-isopropyl-4-methyl-5-oxo-2-imidazolin-2-yl)-benzoic acid; | 8.000 | 8.0 | 9.0 | 8.0 | 9.0 | 9.0 | 5.0 | 7.0 | 9.0 | 3.0 | 3.0 | |
| | 2.000 | 3.0 | 0.0 | 0.0 | 9.0 | 9.0 | 3.0 | 3.0 | 3.0 | 0.0 | 0.0 | |
| | 1.000 | 0.0 | 0.0 | 0.0 | 6.0 | 6.0 | 0.0 | 0.0 | 0.0 | 0.0 | 0.0 | |
| 3-(4-Isopropyl-4-methyl-5-oxo-2-imidazolin-2-yl)-2-naphthoic acid hydrochloride. | 2.000 | 8.0 | 6.0 | 9.0 | 9.0 | 9.0 | 0.0 | 4.0 | 9.0 | 9.0 | 4.0 | |
| | 1.000 | 3.0 | 2.0 | 8.0 | 9.0 | 5.0 | 0.0 | 3.0 | 6.0 | 5.0 | 2.0 | |
| | .500 | 0.0 | 0.0 | 2.0 | 2.0 | 0.0 | 0.0 | 0.0 | 0.0 | 5.0 | 1.0 | |
| Methyl 2-(4-isopropyl-4-methyl-5-oxo-2-imidazolin-2-yl)-4,5-dimethylbenzoate; | 10.000 | 2.0 | 1.0 | 9.0 | | | 1.0 | 2.0 | 0.0 | | | 0.0 |
| | 2.000 | 0.0 | | 8.0 | | | | | 0.0 | | | 0.0 |
| | 1.000 | 0.0 | | 6.0 | | | | | | | | |
| 2-Propynyl 2(4-isopropyl-4-methyl-5-oxo-2-imidazolin-2-yl)-4,5-dimethylbenzoate; | 10.000 | 9.0 | 0.0 | 9.0 | | 9.0 | 3.0 | 8.0 | 6.0 | 8.0 | 0.0 | 0.0 |
| | 2.000 | 7.3 | 8.0 | 8.7 | 4.5 | 8.5 | 5.0 | 7.5 | 5.0 | 6.0 | 0.0 | 0.0 |
| | 1.000 | 3.3 | 8.0 | 8.3 | 4.5 | 9.0 | 6.0 | 7.5 | 4.7 | 4.0 | 0.0 | 0.0 |
| | .500 | 0.7 | 3.0 | 6.7 | 4.5 | 8.0 | 1.0 | 5.5 | 2.7 | 3.5 | 0.0 | 0.0 |
| | .250 | 0.0 | 2.0 | 5.0 | 4.5 | 6.5 | 0.0 | 2.0 | 0.0 | 0.0 | 0.0 | 0.0 |
| | .125 | 0.0 | 0.0 | 4.0 | 0.0 | | 0.0 | 2.5 | 0.0 | | | 0.0 |
| Ethyl 2-(4-isopropyl-4-methyl-5-oxo-2-imidazolin-2-yl)-4,5-dimethylbenzoate; | 2.000 | 0.0 | | 8.0 | | | | | 0.0 | | | |
| | 1.000 | 0.0 | | 7.0 | | | | | 0.0 | | | |
| | .500 | 0.0 | | 6.0 | | | | | 0.0 | | | |
| | .250 | 0.0 | | 3.0 | | | | | 0.0 | | | |
| 2-(4-Isopropyl-4-methyl-5-oxo-2-imidazolin-2-yl)-4,5-dimethylbenzoic acid; | 10.000 | 9.0 | 9.0 | 9.0 | 8.0 | | 7.0 | 8.0 | 8.0 | | | 3.0 |
| | 2.000 | 7.0 | | 8.0 | 0.0 | | | | 7.0 | | | 3.0 |
| | 1.000 | 0.0 | | 3.0 | | | | | | | | |
| 2-(4-isopropyl-4-methyl-5-oxo-2-imidazolin-2-yl)-4,5-dimethylbenzoic acid hydrochloride; | 10.000 | 9.0 | 9.0 | 9.0 | | | 7.0 | 8.0 | | 9.0 | 0.0 | 0.0 |
| | 2.000 | 8.0 | 9.0 | 8.0 | | | 7.0 | 6.0 | | 9.0 | 0.0 | 0.0 |
| | 1.000 | 7.0 | 9.0 | 8.0 | | | 6.0 | 5.0 | | 7.0 | 0.0 | 0.0 |
| | .500 | 5.0 | 8.0 | 8.0 | | | 5.0 | 0.0 | | 5.0 | 0.0 | 0.0 |
| | .250 | 3.0 | 7.0 | 5.0 | | | 5.0 | 7.0 | | 5.0 | 0.0 | 0.0 |
| | .125 | 0.0 | 1.0 | 1.0 | | | 3.0 | 0.0 | | 3.0 | 0.0 | 0.0 |
| Methyl 2-(4-Isopropyl-4-methyl-5-oxo-2-imidazolin-2-yl)-3,5-dimethylbenzoate; | 2.000 | 6.0 | 3.0 | 4.0 | 9.0 | 9.0 | 6.0 | 7.0 | 0.0 | 3.0 | 0.0 | |
| | 1.000 | 3.0 | 0.0 | 3.0 | 0.0 | 9.0 | 2.0 | 3.0 | 0.0 | 2.0 | 0.0 | |
| | .500 | 3.0 | 0.0 | 0.0 | 0.0 | 5.0 | 0.0 | 0.0 | 0.0 | 1.0 | 0.0 | |
| | .250 | 0.0 | 0.0 | 0.0 | 0.0 | 5.0 | 0.0 | 0.0 | 0.0 | 0.0 | 0.0 | |
| 2-(4-Isopropyl-4-methyl-5-oxo-2-imidazolin-2-yl)-3,5-dimethylbenzoic acid; | 2.000 | 9.0 | 9.0 | 8.0 | 9.0 | 9.0 | 8.0 | 8.0 | 9.0 | 8.0 | 8.0 | |
| | 1.000 | 9.0 | 9.0 | 8.0 | 9.0 | 9.0 | 8.0 | 8.0 | 9.0 | 8.0 | 7.0 | |
| | .500 | 7.0 | 9.0 | 6.0 | 9.0 | 9.0 | 8.0 | 8.0 | 5.0 | 7.0 | 4.0 | |
| | .250 | 6.0 | 8.0 | 5.0 | 9.0 | 9.0 | 8.0 | 7.0 | 5.0 | 5.0 | 3.0 | |

TABLE III-continued

PRE-EMERGENCE TESTS - RATES IN KG/HA

| Compound | RATE | BARNY ARDGR | P NUT SEDGE | WILD OATS | QUACK GRASS | FLD B INDWD | MRNGL RY SP | VELVE TLEAF | S BAR LY LA | CORN FIELD | SOYBE AN WI | WHE AT ER |
|---|---|---|---|---|---|---|---|---|---|---|---|---|
| 2-(4-Isopropyl-4-methyl-5-oxo-2-imidazolin-2-yl)-3,4-dimethylbenzoic acid; | .125 | 3.0 | 8.0 | 4.0 | 9.0 | 9.0 | 8.0 | 7.0 | 1.0 | 4.0 | 2.0 | |
| | .063 | 2.0 | 5.0 | 2.0 | 6.0 | 9.0 | 7.0 | 4.0 | 0.0 | 2.0 | 1.0 | |
| | 2.000 | 9.0 | 9.0 | 8.0 | 9.0 | 9.0 | 8.0 | 8.0 | 8.0 | 9.0 | 5.0 | |
| | 1.000 | 9.0 | 9.0 | 6.0 | 9.0 | 9.0 | 8.0 | 8.0 | 4.0 | 9.0 | 4.0 | |
| | .500 | 7.0 | 7.0 | 5.0 | 9.0 | 9.0 | 8.0 | 7.0 | 0.0 | 9.0 | 3.0 | |
| | .250 | 4.0 | 5.0 | 3.0 | 6.0 | 9.0 | 8.0 | 3.0 | 0.0 | 6.0 | 3.0 | |
| | .125 | 4.0 | 0.0 | 2.0 | 0.0 | 7.0 | 6.0 | 3.0 | 0.0 | 2.0 | 1.0 | |
| Methyl 2-(4-isopropyl-4-methyl-5-oxo-2-imidazolin-2-yl)-3,4-dimethylbenzoic acid; | 2.000 | 5.0 | 0.0 | 0.0 | 0.0 | 9.0 | 5.0 | 5.0 | 0.0 | 4.0 | 0.0 | |
| | 1.000 | 4.0 | 0.0 | 0.0 | 0.0 | 4.0 | 4.0 | 1.0 | 0.0 | 0.0 | 0.0 | |
| | .500 | 0.0 | 0.0 | 0.0 | 0.0 | 3.0 | 3.0 | 0.0 | 0.0 | 0.0 | 0.0 | |
| | .250 | 0.0 | 0.0 | 0.0 | 0.0 | 0.0 | 1.0 | 0.0 | 0.0 | 0.0 | 0.0 | |
| Methyl 3-(dimethylamino)-2-(4-isopropyl-4-methyl-5-oxo-2-imidazolin-2-yl)-benzoate; | 1.000 | 0.0 | 0.0 | 0.0 | 0.0 | 9.0 | 0.0 | 0.0 | 0.0 | 3.0 | 0.0 | |
| | .500 | 0.0 | 0.0 | 0.0 | 0.0 | 3.0 | 0.0 | 0.0 | 0.0 | 0.0 | 0.0 | |
| 5-Chloro-2-(4-isopropyl-4-methyl-5-oxo-2-imidazolin-2-yl)-p-toluic acid; | 2.000 | 9.0 | 8.0 | 8.0 | 9.0 | 9.0 | 7.0 | 7.0 | 6.0 | 8.0 | 5.0 | |
| | 1.000 | 9.0 | 3.0 | 6.0 | 9.0 | 9.0 | 6.0 | 7.0 | 3.0 | 8.0 | 4.0 | |
| | .500 | 6.0 | 0.0 | 3.0 | 5.0 | 9.0 | 0.0 | 4.0 | 2.0 | 5.0 | 0.0 | |
| | .250 | 4.0 | 0.0 | 2.0 | 0.0 | 9.0 | 0.0 | 2.0 | 1.0 | 4.0 | 0.0 | |
| | .125 | 4.0 | 0.0 | 0.0 | 0.0 | 9.0 | 0.0 | 2.0 | 0.0 | 2.0 | 0.0 | |
| | .063 | 2.0 | 0.0 | 0.0 | 0.0 | 9.0 | 0.0 | 1.0 | 0.0 | 1.0 | 0.0 | |
| Methyl 6-(4-isopropyl-4-methyl-5-oxo-2-imidazolin-2-yl)-m-anisate; | 2.000 | 0.0 | 8.0 | 9.0 | 9.0 | 9.0 | 0.0 | 6.0 | 0.0 | 0.0 | 5.0 | |
| | 1.000 | 0.0 | 0.0 | 8.0 | 0.0 | 9.0 | 0.0 | 3.0 | 0.0 | 0.0 | 3.0 | |
| | .500 | 0.0 | 0.0 | 8.0 | 0.0 | 0.0 | 0.0 | 0.0 | 0.0 | 0.0 | 1.0 | |
| | .250 | 0.0 | 0.0 | 0.0 | 0.0 | 0.0 | 0.0 | 0.0 | 0.0 | 0.0 | 0.0 | |
| 6-(4-isopropyl-4-methyl-5-oxo-2-imidazolin-2-yl)-m-anisic acid; | 2.000 | 8.0 | 9.0 | 8.0 | 9.0 | 9.0 | 8.0 | 9.0 | 9.0 | 9.0 | 9.0 | |
| | 1.000 | 7.0 | 9.0 | 6.0 | 9.0 | 9.0 | 7.0 | 9.0 | 9.0 | 8.0 | 9.0 | |
| | .500 | 4.0 | 9.0 | 5.0 | 9.0 | 9.0 | 6.0 | 8.0 | 5.0 | 6.0 | 7.0 | |
| | .250 | 3.0 | 0.0 | 3.0 | 0.0 | 5.0 | 3.0 | 4.0 | 1.0 | 5.0 | 4.0 | |
| | .125 | 2.0 | 0.0 | 0.0 | 7.0 | 3.0 | 0.0 | 2.0 | 0.0 | 2.0 | 3.0 | |
| | .063 | 0.0 | 0.0 | 0.0 | 0.0 | 0.0 | 0.0 | 0.0 | 0.0 | 1.0 | 2.0 | |
| 3-Chloro-2-(4-Isopropyl-4-methyl-5-oxo-2-imidazolin-2-yl)-p-toluic acid; | 2.000 | 6.0 | 8.0 | 4.0 | 9.0 | 9.0 | 8.0 | 8.0 | 3.0 | 9.0 | 9.0 | |
| | 1.000 | 2.0 | 8.0 | 3.0 | 6.0 | 9.0 | 9.0 | 8.0 | 2.0 | 5.0 | 5.0 | |
| | .500 | 0.0 | 3.0 | 1.0 | 3.0 | 9.0 | 7.0 | 5.0 | 0.0 | 3.0 | 4.0 | |
| | .250 | 0.0 | 0.0 | 0.0 | 0.0 | 9.0 | 7.0 | 4.0 | 0.0 | 3.0 | 2.0 | |
| | .125 | 0.0 | 0.0 | 0.0 | 0.0 | 7.0 | 0.0 | 2.0 | 0.0 | 1.0 | 0.0 | |
| Benzyl 2-(4-isopropyl-4-methyl-5-oxo-2-imidazolin-2-yl)-4,5-dimethylbenzoate; | 2.000 | 8.0 | 3.0 | 4.0 | 0.0 | 9.0 | 0.0 | 5.0 | 0.0 | 0.0 | 0.0 | |
| | 1.000 | 6.0 | 0.0 | 2.0 | 0.0 | 0.0 | 0.0 | 0.0 | 0.0 | 0.0 | 0.0 | |
| Furfuryl 2-(4-isopropyl-4-methyl-5-oxo-2-imidazolin-2-yl)-4,5-dimethylbenzoate; | 2.000 | 9.0 | 9.0 | 9.0 | 9.0 | 9.0 | 7.0 | 9.0 | 9.0 | 8.0 | 7.0 | |
| | 1.000 | 9.0 | 6.0 | 9.0 | 9.0 | 9.0 | | 8.0 | 9.0 | 7.0 | | |
| | .500 | 6.0 | 3.0 | 5.0 | 5.0 | 0.0 | 7.0 | 8.0 | 5.0 | 4.0 | 3.0 | |
| | .250 | 6.0 | 2.0 | 5.0 | 2.0 | 0.0 | 5.0 | 4.0 | 3.0 | 4.0 | 3.0 | |
| | .125 | 5.0 | 0.0 | 2.0 | 0.0 | 0.0 | 0.0 | 4.0 | 2.0 | 3.0 | 1.0 | |
| | .063 | 2.0 | 0.0 | 0.0 | 0.0 | 0.0 | 0.0 | 2.0 | 0.0 | 2.0 | 1.0 | |
| Isopropylammonium 2-(4-isopropyl-4-methyl-5-oxo-2-imidazolin-2-yl)-4,5-dimethylbenzoic acid; | 2.000 | 9.0 | 9.0 | 9.0 | 9.0 | 9.0 | 8.0 | 8.0 | 9.0 | 9.0 | 6.0 | |
| | 1.000 | 9.0 | 7.0 | 9.0 | 9.0 | 9.0 | 8.0 | 8.0 | 9.0 | 6.0 | 5.0 | |
| | .500 | 9.0 | 8.0 | 9.0 | 9.0 | 9.0 | 7.0 | 8.0 | 9.0 | 5.0 | 2.0 | |
| | .250 | 4.0 | 5.0 | 4.0 | 9.0 | 9.0 | 3.0 | 6.0 | 6.0 | 4.0 | 0.0 | |
| | .125 | 2.0 | 3.0 | 2.0 | 3.0 | 9.0 | 0.0 | 5.0 | 1.0 | 2.0 | 0.0 | |

TABLE III-continued

PRE-EMERGENCE TESTS - RATES IN KG/HA

| Compound | RATE | BARNY ARDGR | P NUT SEDGE | WILD OATS | QUACK GRASS | FLD B INDWD | MRNGL RY SP | VELVE TLEAF | S BAR LY LA | CORN FIELD | SOYBE AN WI | WHE AT ER |
|---|---|---|---|---|---|---|---|---|---|---|---|---|
| 5,6,7,8-Tetrahydro-3-(4-isopropyl-4-methyl-5-oxo-2-imidazolin-2-yl)-2-naphthoic acid; | .063 | 1.0 | 0.0 | 1.0 | 1.0 | 2.0 | 0.0 | 1.0 | 0.0 | 1.0 | 0.0 | |
|  | 2.000 | 6.0 | 0.0 | 3.0 | 8.0 | 9.0 | 7.0 | 6.0 | 0.0 | 7.0 | 0.0 | |
|  | 1.000 | 0.0 | 0.0 | 0.0 | 4.0 | 0.0 | 3.0 | 3.0 | 0.0 | 7.0 | 0.0 | |
| 2-(4-Isopropyl-4-methyl-5-oxo-2-imidazolin-2-yl)-4,6-dimethylbenzoic acid; | 2.000 | 7.0 | 9.0 | 0.0 | 5.0 | 9.0 | 3.0 | 8.0 | 3.0 | 3.0 | 8.0 | |
|  | 1.000 | 5.0 | 7.0 | 0.0 | 4.0 | 9.0 | 5.0 | 7.0 | 3.0 | 2.0 | 7.0 | |
|  | .500 | 5.0 | 5.0 | 0.0 | 0.0 | 9.0 | 2.0 | 5.0 | 2.0 | 0.0 | 6.0 | |
|  | .250 | 2.0 | 1.0 | 0.0 | 0.0 | 6.0 | 0.0 | 3.0 | 2.0 | 0.0 | 5.0 | |
| 2-Propynyl 2-(4-isopropyl-4-methyl-5-oxo-2-imidazolin-2-yl)-4,5-dimethylbenzoate; | 2.000 | 6.0 | 7.0 | 0.0 | 4.0 | 9.0 | 4.0 | 5.0 | 0.0 | 0.0 | 5.0 | |
|  | 1.000 | 5.0 | 6.0 | 0.0 | 0.0 | 5.0 | 3.0 | 4.0 | 0.0 | 0.0 | 4.0 | |
|  | .500 | 4.0 | 0.0 | 0.0 | 0.0 | 0.0 | 1.0 | 3.0 | 0.0 | 0.0 | 3.0 | |
| 5-Chloro-6-(5-isopropyl-5-methyl-4-oxo-2-imidazolin-2-yl)-m-toluic acid; | 2.000 | 6.0 | 5.0 | 7.0 | 9.0 | 9.0 | 8.0 | 8.0 | 7.0 | 5.0 | 6.0 | |
|  | 1.000 | 3.0 | 3.0 | 3.0 | 8.0 | 9.0 | 6.0 | 5.0 | 2.0 | 3.0 | 6.0 | |
|  | .500 | 2.0 | 0.0 | 2.0 | 6.0 | 9.0 | 5.0 | 5.0 | 0.0 | 2.0 | 2.0 | |
|  | .250 | 0.0 | 0.0 | 0.0 | 0.0 | 9.0 | 3.0 | 3.0 | 0.0 | 1.0 | 0.0 | |
|  | .125 | 0.0 | 0.0 | 0.0 | 0.0 | 9.0 | 3.0 | 0.0 | 0.0 | 0.0 | 0.0 | |
|  | .063 | 0.0 | 0.0 | 0.0 | 0.0 | 9.0 | 2.0 | 0.0 | 0.0 | 0.0 | 0.0 | |
| Methyl 4,5-dichloro-2-(4-isopropyl-4-methyl-5-oxo-2-imidazolin-2-yl)benzoate; 4,5-Dichloro-2-(4-isopropyl-4-methyl-5-oxo-2-imidazolin-2-yl)benzoic acid; | | | | | | | | | | | | |
| Methyl 3-Chloro-2-(4-isopropyl-4-methyl-5-oxo-2-imidazolin-2-yl)-p-toluate; | 2.000 | 0.0 | 0.0 | 0.0 | 0.0 | 9.0 | 6.0 | 3.0 | 0.0 | 0.0 | 0.0 | |
|  | 1.000 | 0.0 | 0.0 | 0.0 | 0.0 | 6.0 | 5.0 | 3.0 | 0.0 | 0.0 | 0.0 | |
|  | .500 | 0.0 | 0.0 | 0.0 | 0.0 | 6.0 | 3.0 | 2.0 | 0.0 | 0.0 | 0.0 | |
|  | .250 | 0.0 | 0.0 | 0.0 | 0.0 | 3.0 | 2.0 | 0.0 | 0.0 | 0.0 | 0.0 | |

EXAMPLE 23

Postemergence herbicidal evaluation of test compounds

The postemergence herbicidal activity of test compounds is determined utilizing the procedure of Example 21, excepting that test compounds are applied at rates of application between 0.063 and 2.0 kg/ha and Green Foxtail (*Setaria viridis*) and Sunflowers (*Helianthus annus*) are substituted for barley and soybeans. Data obtained are reported in Table IV below.

TABLE IV

POST-EMERGENCE TESTS - RATES IN KG/HA

| Compound | RATE | BARN-YARD-GR | GREEN FOX | P NUT SEDGE | WILD OATS | QUACK GRASS | FLD B INDWD | MRN-GLRY SP | VEL-VET LEAF | CORN FIELD | SUN-FLR XXX |
|---|---|---|---|---|---|---|---|---|---|---|---|
| 2-(4-Isopropyl-4-methyl- | 2.000 | 5.0 | 6.0 | 8.0 | 9.0 | 8.0 | 9.0 | 0.0 | 3.0 | 7.0 | 9.0 |
| 5-oxo-2-imidazolin-2-yl)- | 1.000 | 4.0 | 6.0 | 7.0 | 9.0 | 6.0 | 0.0 | 0.0 | 2.0 | 3.0 | 9.0 |
| 3,6-dimethylbenzoic acid | .500 | 3.0 | 6.0 | 5.0 | 9.0 | 6.0 | 0.0 | 0.0 | 1.0 | 2.0 | 9.0 |
|  | .250 | 0.0 | 3.0 | 2.0 | 6.0 | 2.0 | 0.0 | 0.0 | 0.0 | 1.0 | 9.0 |
|  | .125 | 0.0 | 0.0 | 0.0 | 4.0 | 1.0 | 0.0 | 0.0 | 0.0 | 0.0 | 9.0 |
|  | .063 | 0.0 | 0.0 | 0.0 | 0.0 | 0.0 | 0.0 | 0.0 | 0.0 | 0.0 | 5.0 |
| 3-Fluoro-2-(4-isopropyl- | 1.000 | 0.0 | 5.0 | 0.0 | 0.0 | 0.0 | 9.0 | 6.0 | 6.0 | 6.0 | 9.0 |
| 4-methyl-5-oxo-2-imidazo- | .500 | 0.0 | 3.0 | 0.0 | 0.0 | 0.0 | 9.0 | 5.0 | 2.0 | 3.0 | 8.0 |
| lin-2-yl)-p-toluic acid | .250 | 0.0 | 0.0 | 0.0 | 0.0 | 0.0 | 4.0 | 2.0 | 0.0 | 2.0 | 9.0 |
|  | .125 | 0.0 | 0.0 | 0.0 | 0.0 | 0.0 | 3.0 | 0.0 | 0.0 | 0.0 | 5.0 |
|  | .063 | 0.0 | 0.0 | 0.0 | 0.0 | 0.0 | 0.0 | 0.0 | 0.0 | 0.0 | 3.0 |
| Methyl 3-fluoro-2-(4- | 2.000 | 3.0 | 7.0 | 0.0 | 0.0 | 0.0 | 0.0 | 7.0 | 4.0 | 0.0 | 0.0 |
| isopropyl-4-methyl-5- | 1.000 | 2.0 | 3.0 | 0.0 | 0.0 | 0.0 | 0.0 | 6.0 | 3.0 | 0.0 | 0.0 |
| oxo-2-imidazolin-2-yl)- | .500 | 0.0 |  | 0.0 | 0.0 | 0.0 | 0.0 | 5.0 | 2.0 | 0.0 | 0.0 |
| p-toluate | .250 | 0.0 | 0.0 | 0.0 | 0.0 | 0.0 | 0.0 | 4.0 | 0.0 | 0.0 | 0.0 |
|  | .125 | 0.0 | 0.0 | 0.0 | 0.0 | 0.0 | 0.0 | 3.0 | 0.0 | 0.0 | 0.0 |
|  | .063 | 0.0 | 0.0 | 0.0 | 0.0 | 0.0 | 0.0 | 2.0 | 0.0 | 0.0 | 0.0 |
| Methyl 5-(4-isopropyl-4- | 2.000 | 0.0 | 0.0 | 0.0 | 6.0 | 0.0 | 0.0 | 0.0 | 0.0 | 0.0 | 0.0 |
| methyl-5-oxo-2-imidazolin- | 1.000 | 0.0 | 0.0 | 0.0 | 4.0 | 0.0 | 0.0 | 0.0 | 0.0 | 0.0 | 0.0 |
| 2-yl)-4-indancarboxylate | .500 | 0.0 | 0.0 | 0.0 | 2.0 | 0.0 | 0.0 | 0.0 | 0.0 | 0.0 | 0.0 |
|  | .250 | 0.0 | 0.0 | 0.0 | 0.0 | 0.0 | 0.0 | 0.0 | 0.0 | 0.0 | 0.0 |
|  | .125 | 0.0 | 0.0 | 0.0 | 0.0 | 0.0 | 0.0 | 0.0 | 0.0 | 0.0 | 0.0 |
|  | .063 | 0.0 | 0.0 | 0.0 | 0.0 | 0.0 | 0.0 | 0.0 | 0.0 | 0.0 | 0.0 |
| 6-(4-Isopropyl-4-methyl- | 2.000 | 0.0 | 0.0 | 0.0 | 0.0 | 0.0 | 0.0 | 0.0 | 0.0 | 8.0 | 0.0 |
| 5-oxo-2-imidazolin-2-yl)- | 1.000 | 0.0 | 0.0 | 0.0 | 0.0 | 0.0 | 0.0 | 0.0 | 0.0 | 7.0 | 0.0 |
| 5-indancarboxylic acid | .500 | 0.0 | 0.0 | 0.0 | 0.0 | 0.0 | 0.0 | 0.0 | 0.0 | 6.0 | 0.0 |
|  | .250 | 0.0 | 0.0 | 0.0 | 0.0 | 0.0 | 0.0 | 0.0 | 0.0 | 2.0 | 0.0 |
|  | .125 | 0.0 | 0.0 | 0.0 | 0.0 | 0.0 | 0.0 | 0.0 | 0.0 | 2.0 | 0.0 |
|  | .063 | 0.0 | 0.0 | 0.0 | 0.0 | 0.0 | 0.0 | 0.0 | 0.0 | 2.0 | 0.0 |
| 5-(4-Isopropyl-4-methyl- | .500 | 0.0 | 0.0 | 0.0 | 0.0 | 0.0 | 0.0 | 0.0 | 0.0 | 0.0 | 0.0 |
| 5-oxo-2-imidazolin-2-yl)- | .250 | 0.0 | 0.0 | 0.0 | 0.0 | 0.0 | 0.0 | 0.0 | 0.0 | 0.0 | 0.0 |
| 4-indancarboxylic acid | .125 | 0.0 | 0.0 | 0.0 | 0.0 | 0.0 | 0.0 | 0.0 | 0.0 | 0.0 | 0.0 |
|  | .063 | 0.0 | 0.0 | 0.0 | 0.0 | 0.0 | 0.0 | 0.0 | 0.0 | 0.0 | 0.0 |
| 4-(4-Isopropyl-4-methyl- | 2.000 | 9.0 | 8.0 | 3.0 | 7.0 | 0.0 | 9.0 | 8.0 | 8.0 | 4.0 | 8.0 |
| 5-oxo-2-imidazolin-2-yl)- | 1.000 | 9.0 | 7.0 | 3.0 | 4.0 | 0.0 | 9.0 | 6.0 | 9.0 | 4.0 | 8.0 |
| bicyclo[4.2.0]octa-1,3,5- | .500 | 9.0 | 7.0 | 0.0 | 3.0 | 0.0 | 9.0 | 4.0 | 9.0 | 3.0 | 6.0 |
| triene-3-carboxylic acid | .250 | 9.0 | 5.0 | 0.0 | 2.0 | 0.0 | 7.0 | 3.0 | 9.0 | 2.0 | 6.0 |
|  | .125 | 9.0 | 3.0 | 0.0 | 0.0 | 0.0 | 7.0 | 0.0 | 7.0 | 1.0 | 4.0 |
|  | .063 | 7.0 | 2.0 | 0.0 | 0.0 | 0.0 | 6.0 | 0.0 | 5.0 | 1.0 | 2.0 |
| 4-(4-Isopropyl-4-methyl- | 2.000 | 6.0 | 0.0 | 0.0 | 5.0 | 0.0 | 7.0 | 0.0 | 5.0 | 3.0 | 0.0 |
| 5-oxo-2-imidazolin-2-yl)- | 1.000 | 3.0 | 0.0 | 0.0 | 2.0 | 0.0 | 6.0 | 0.0 | 3.0 | 3.0 | 0.0 |
| bicyclo[4.2.0]octa-1,3,5- | .500 | 3.0 | 0.0 | 0.0 | 0.0 | 0.0 | 5.0 | 0.0 | 2.0 | 3.0 | 0.0 |
| triene-3-carboxylate | .250 | 0.0 | 0.0 | 0.0 | 0.0 | 0.0 | 3.0 | 0.0 | 0.0 | 2.0 | 0.0 |
|  | .125 | 0.0 | 0.0 | 0.0 | 0.0 | 0.0 | 2.0 | 0.0 | 0.0 | 1.0 | 0.0 |
|  | .063 | 0.0 | 0.0 | 0.0 | 0.0 | 0.0 | 0.0 | 0.0 | 0.0 | 1.0 | 0.0 |
| Methyl 2-(4-isopropyl- | 2.000 | 0.0 | 0.0 | 0.0 | 0.0 | 0.0 | 6.0 | 8.0 | 7.0 | 0.0 | 0.0 |
| 4-methyl-5-oxo-2-imida- | 1.000 | 0.0 | 0.0 | 0.0 | 0.0 | 0.0 | 6.0 | 7.0 | 2.0 | 0.0 | 0.0 |
| zolin-2-yl)-3-(methyl- | .500 | 0.0 | 0.0 | 0.0 | 0.0 | 0.0 | 5.0 | 8.0 | 0.0 | 0.0 | 0.0 |
| thio)benzoate | .250 | 0.0 | 0.0 | 0.0 | 0.0 | 0.0 | 4.0 | 8.0 | 0.0 | 0.0 | 0.0 |
|  | .125 | 0.0 | 0.0 | 0.0 | 0.0 | 0.0 | 3.0 | 7.0 | 0.0 | 0.0 | 0.0 |
|  | .063 | 0.0 | 0.0 | 0.0 | 0.0 | 0.0 | 2.0 | 5.0 | 0.0 | 0.0 | 0.0 |
| Methyl α-fluoro-6-(4- | 2.000 | 0.0 | 0.0 | 0.0 | 0.0 | 0.0 | 0.0 | 0.0 | 0.0 | 2.0 | 0.0 |
| isopropyl-4-methyl-5- | 1.000 | 0.0 | 0.0 | 0.0 | 0.0 | 0.0 | 0.0 | 0.0 | 0.0 | 0.0 | 0.0 |
| oxo-2-imidazolin-2- | .500 | 0.0 | 0.0 | 0.0 | 0.0 | 0.0 | 0.0 | 0.0 | 0.0 | 0.0 | 0.0 |
| yl)-m-toluate | .250 | 0.0 | 0.0 | 0.0 | 0.0 | 0.0 | 0.0 | 0.0 | 0.0 | 0.0 | 0.0 |
|  | .125 | 0.0 | 0.0 | 0.0 | 0.0 | 0.0 | 0.0 | 0.0 | 0.0 | 0.0 | 0.0 |
|  | .063 | 0.0 | 0.0 | 0.0 | 0.0 | 0.0 | 0.0 | 0.0 | 0.0 | 0.0 | 0.0 |
| 2-(4-Isopropyl-4- | 2.000 | 0.0 | 0.0 | 0.0 | 0.0 | 0.0 | 6.0 | 7.0 | 0.0 | 0.0 | 0.0 |
| methyl-5-oxo-2-imida- | 1.000 | 0.0 | 0.0 | 0.0 | 0.0 | 0.0 | 3.0 | 4.0 | 0.0 | 0.0 | 0.0 |
| zolin-2-yl)-3-(methyl- | .500 | 0.0 | 0.0 | 0.0 | 0.0 | 0.0 | 3.0 | 2.0 | 0.0 | 0.0 | 0.0 |
| thio)benzoic acid | .250 | 0.0 | 0.0 | 0.0 | 0.0 | 0.0 | 0.0 | 0.0 | 0.0 | 0.0 | 0.0 |
|  | .125 | 0.0 | 0.0 | 0.0 | 0.0 | 0.0 | 0.0 | 0.0 | 0.0 | 0.0 | 0.0 |
|  | .063 | 0.0 | 0.0 | 0.0 | 0.0 | 0.0 | 0.0 | 0.0 | 0.0 | 0.0 | 0.0 |
| α-Fluoro-6-(4-isopro- | 2.000 | 0.0 | 0.0 | 0.0 | 0.0 | 0.0 | 3.0 | 3.0 | 3.0 | 0.0 | 0.0 |
| pyl-4-methyl-5-oxo-2- | 1.000 | 0.0 | 0.0 | 0.0 | 0.0 | 0.0 | 4.0 | 0.0 | 2.0 | 0.0 | 0.0 |
| imidazolin-2-yl)-m- | .500 | 0.0 | 0.0 | 0.0 | 0.0 | 0.0 | 5.0 | 0.0 | 0.0 | 0.0 | 0.0 |
| toluic acid | .250 | 0.0 | 0.0 | 0.0 | 0.0 | 0.0 | 4.0 | 0.0 | 0.0 | 0.0 | 0.0 |
|  | .125 | 0.0 | 0.0 | 0.0 | 0.0 | 0.0 | 5.0 | 0.0 | 0.0 | 0.0 | 0.0 |
|  | .063 | 0.0 | 0.0 | 0.0 | 0.0 | 0.0 | 2.0 | 0.0 | 0.0 | 0.0 | 0.0 |
| Methyl α,α-difluoro-6- | 2.000 | 0.0 | 3.0 | 0.0 | 0.0 | 0.0 | 0.0 | 3.0 | 3.0 | 0.0 | 0.0 |
| (4-isopropyl-4-methyl- | 1.000 | 0.0 | 2.0 | 0.0 | 0.0 | 0.0 | 0.0 | 2.0 | 0.0 | 0.0 | 0.0 |

TABLE IV-continued

POST-EMERGENCE TESTS - RATES IN KG/HA

| Compound | RATE | BARN-YARD-GR | GREEN FOX | P NUT SEDGE | WILD OATS | QUACK GRASS | FLD B INDWD | MRN-GLRY SP | VEL-VET LEAF | CORN FIELD | SUN-FLR XXX |
|---|---|---|---|---|---|---|---|---|---|---|---|
| 5-oxo-2-imidazolin-2-yl)-m-anisate and methyl α,α-difluoro-2-(4-isopropyl-4-methyl-5-oxo-2-imidazolin-2-yl)-p-anisate | .500 | 0.0 | 0.0 | 0.0 | 0.0 | 0.0 | 0.0 | 0.0 | 0.0 | 0.0 | 0.0 |
| | .250 | 0.0 | 0.0 | 0.0 | 0.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| α,α-Difluoro-6-(4-isopropyl-4-methyl-5-oxo-2-imidazolin-2-yl)-m-acid and α,α-difluoro-2-(4-isopropyl-4-methyl-5-oxo-2-imidazolin-2-yl)-p-anisic acid | 2.000 | 0.0 | 4.0 | 0.0 | 0.0 | 0.0 | 8.0 | 8.0 | 7.0 | 0.0 | 6.0 |
| | 1.000 | 0.0 | 3.0 | 0.0 | 0.0 | 0.0 | 7.0 | 3.0 | 4.0 | 0.0 | 6.0 |
| | .500 | 0.0 | 2.0 | 0.0 | 0.0 | 0.0 | 5.0 | 2.0 | 2.0 | 0.0 | 4.0 |
| | .250 | 0.0 | 0.0 | 0.0 | 0.0 | 0.0 | 5.0 | 0.0 | 0.0 | 0.0 | 3.0 |
| | .125 | 0.0 | 0.0 | 0.0 | 0.0 | 0.0 | 2.0 | 0.0 | 0.0 | 0.0 | 2.0 |
| | .063 | 0.0 | 0.0 | 0.0 | 0.0 | 0.0 | 0.0 | 0.0 | 0.0 | 0.0 | 2.0 |
| Methyl α-fluoro-2-(4-isopropyl-4-methyl-5-oxo-2-imidazolin-2-yl)-p-toluate | 2.000 | 7.0 | 6.0 | 0.0 | 8.0 | 0.0 | 6.0 | 0.0 | 4.0 | 0.0 | 0.0 |
| | 1.000 | 3.0 | 2.0 | 0.0 | 3.0 | 0.0 | 4.0 | 0.0 | 2.0 | 0.0 | 0.0 |
| | .500 | 2.0 | 0.0 | 0.0 | 2.0 | 0.0 | 2.0 | 0.0 | 2.0 | 0.0 | 0.0 |
| | .250 | 0.0 | 0.0 | 0.0 | 0.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| Methyl α,α-trifluoro-6-(4-isopropyl-4-methyl-5-oxo-2-imidazolin-2-yl)-m-anisate | 2.000 | 0.0 | 0.0 | 0.0 | 8.0 | 0.0 | 0.0 | 3.0 | 3.0 | 3.0 | 2.0 |
| | 1.000 | 0.0 | 0.0 | 0.0 | 3.0 | 0.0 | 0.0 | 0.0 | 0.0 | 2.0 | 2.0 |
| | .500 | 0.0 | 0.0 | 0.0 | 3.0 | 0.0 | 0.0 | 0.0 | 0.0 | 2.0 | 2.0 |
| | .250 | 0.0 | 0.0 | 0.0 | 2.0 | 0.0 | 0.0 | 0.0 | 0.0 | 1.0 | 0.0 |
| | .125 | 0.0 | 0.0 | 0.0 | 0.0 | 0.0 | 0.0 | 0.0 | 0.0 | 1.0 | 0.0 |
| | .063 | 0.0 | 0.0 | 0.0 | 0.0 | 0.0 | 0.0 | 0.0 | 0.0 | 1.0 | 0.0 |
| α,α,α-trifluoro-6-(4-isopropyl-4-methyl-5-oxo-2-imidazolin-2-yl)-m-anisic acid sodium sulfate | 2.000 | 0.0 | 0.0 | 9.0 | 0.0 | 0.0 | 7.0 | 6.0 | 5.0 | 0.0 | 3.0 |
| | 1.000 | 0.0 | 0.0 | 0.0 | 0.0 | 0.0 | 7.0 | 4.0 | 3.0 | 0.0 | 2.0 |
| | .500 | 0.0 | 0.0 | 0.0 | 0.0 | 0.0 | 2.0 | 2.0 | 2.0 | 0.0 | 0.0 |
| | .250 | 0.0 | 0.0 | 0.0 | 0.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |

EXAMPLE 24

Preemergence herbicidal evaluation of test compounds

The preemergence herbicidal activity of test compounds is determined utilizing the procedure of Example 21, excepting that test compounds are applied at rates of application between 0.063 and 2.0 kg/ha and Green Foxtail (*Setaria viridis*) and Sunflowers (*Helianthus annus*) are substituted for barley and soybeans. Data obtained are reported in Table V below.

TABLE V

PRE-EMERGENCE TESTS - RATES IN KG/HA

| Compound | RATE | BARN-YARD GR | GREEN FOX | P NUT SEDGE | WILD OATS | QUACK GRASS | FLD B INDWD | MRN GLRY SP | VEL-VET LEAF | CORN FIELD | SUN-FLR XXX |
|---|---|---|---|---|---|---|---|---|---|---|---|
| 2-(4-Isopropyl-4-methyl-5-oxo-2-imidazolin-2-yl)-3,6-dimethylbenzoic acid | 2.000 | 6.0 | 9.0 | 9.0 | 9.0 | 9.0 | 9.0 | 8.0 | 8.0 | 8.0 | 9.0 |
| | 1.000 | 2.0 | 9.0 | 9.0 | 9.0 | 9.0 | 9.0 | 6.0 | 6.0 | 8.0 | 9.0 |
| | .500 | 0.0 | 7.0 | 9.0 | 9.0 | 9.0 | 6.0 | 3.0 | 3.0 | 7.0 | 9.0 |
| | .250 | 0.0 | 6.0 | 7.0 | | 5.0 | 4.0 | 2.0 | 2.0 | 2.0 | 8.0 |
| | .125 | 0.0 | 0.0 | 7.0 | 0.0 | | 2.0 | 0.0 | 0.0 | 0.0 | 3.0 |
| | .063 | 0.0 | 0.0 | 2.0 | 0.0 | | 0.0 | 0.0 | 0.0 | 0.0 | 2.0 |
| 3-Fluoro-2-(4-isopropyl-4-methyl-5-oxo-2-imidazolin-2-yl)-p-toluic acid | 1.000 | 0.0 | 0.0 | 0.0 | 7.0 | 0.0 | 0.0 | 0.0 | | 0.0 | 0.0 |
| | .500 | 0.0 | 0.0 | 0.0 | 4.0 | 0.0 | 0.0 | 0.0 | 0.0 | 0.0 | 0.0 |
| | .250 | 0.0 | 0.0 | 0.0 | 3.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| Methyl 3-fluoro-2-(4-isopropyl-4-methyl-5-oxo-2-imidazolin-2-yl)-p-toluate | 2.000 | 8.0 | 7.0 | 8.0 | 6.0 | 3.0 | 9.0 | 8.0 | 8.0 | 8.0 | 0.0 |
| | 1.000 | 8.0 | 7.0 | 5.0 | 4.0 | | 9.0 | 8.0 | 6.0 | 5.0 | 0.0 |
| | .500 | 6.0 | 7.0 | 2.0 | 3.0 | 0.0 | 9.0 | 4.0 | 3.0 | 5.0 | 0.0 |
| | .250 | 4.0 | 6.0 | 0.0 | 2.0 | 0.0 | 7.0 | 4.0 | 0.0 | 2.0 | 0.0 |
| | .125 | 2.0 | 6.0 | 0.0 | 0.0 | | 4.0 | 3.0 | 0.0 | 0.0 | 0.0 |
| | .063 | 0.0 | 4.0 | 0.0 | 0.0 | 0.0 | 2.0 | 2.0 | 0.0 | 0.0 | 0.0 |
| Methyl 5-(4-isopropyl-4-methyl-5-oxo-2-imidazolin-2-yl)-4-indancarboxylate | 2.000 | 7.0 | 0.0 | 0.0 | 8.0 | 0.0 | 6.0 | 0.0 | 0.0 | 0.0 | 0.0 |
| | 1.000 | 2.0 | 0.0 | 0.0 | 8.0 | 0.0 | 4.0 | 0.0 | 0.0 | 0.0 | 0.0 |
| | .500 | 0.0 | 0.0 | 0.0 | 8.0 | 0.0 | 2.0 | 0.0 | 0.0 | 0.0 | 0.0 |
| | .250 | 0.0 | 0.0 | 0.0 | 7.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| 6-(4-Isopropyl-4-methyl-5-oxo-2-imidazolin-2-yl)-5-indancarboxylic acid | 2.000 | 4.0 | 2.0 | 5.0 | 7.0 | 7.0 | 7.0 | 4.0 | 6.0 | 4.0 | 2.0 |
| | 1.000 | 2.0 | 2.0 | 2.0 | 2.0 | 7.0 | 2.0 | 2.0 | 2.0 | 2.0 | 1.0 |
| | .500 | 1.0 | 0.0 | 2.0 | 1.0 | 7.0 | 1.0 | 2.0 | 2.0 | 2.0 | 0.0 |
| | .250 | 0.0 | 0.0 | 1.0 | 0.0 | | 0.0 | 1.0 | 1.0 | 1.0 | 0.0 |
| | .125 | 0.0 | 0.0 | 0.0 | 0.0 | 0.0 | 0.0 | 1.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| 5-(4-Isopropyl-4-methyl- | 1.000 | 8.0 | 3.0 | 2.0 | 1.0 | 0.0 | 4.0 | 0.0 | 5.0 | 4.0 | 1.0 |

TABLE V-continued

PRE-EMERGENCE TESTS - RATES IN KG/HA

| Compound | RATE | BARN-YARD GR | GREEN FOX | P NUT SEDGE | WILD OATS | QUACK GRASS | FLD B INDWD | MRN GLRY SP | VEL-VET LEAF | CORN FIELD | SUN-FLR XXX |
|---|---|---|---|---|---|---|---|---|---|---|---|
| 5-oxo-2-imidazolin-2-yl)-4-indancarboxylic acid | .500 | 3.0 | 2.0 | 1.0 | 0.0 | 0.0 | 0.0 | 0.0 | 3.0 | 2.0 | 0.0 |
| | .250 | 3.0 | 0.0 | 0.0 | 0.0 | 0.0 | 0.0 | 0.0 | 1.0 | 1.0 | 0.0 |
| | .125 | 1.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| 4-(4-Isopropyl-4-methyl-5-oxo-2-imidazolin-2-yl)-bicyclo[4.2.0]octa-1,3,5-triene-3-carboxylic acid | 2.000 | 9.0 | 9.0 | 9.0 | 8.0 | 9.0 | 9.0 | 8.0 | 9.0 | 8.0 | 8.0 |
| | 1.000 | 9.0 | 9.0 | 9.0 | 7.0 | 9.0 | 9.0 | 8.0 | 8.0 | 7.0 | 5.0 |
| | .500 | 9.0 | 9.0 | 8.0 | 5.0 | 9.0 | 9.0 | 6.0 | 8.0 | 7.0 | 6.0 |
| | .250 | 8.0 | 8.0 | 8.0 | 4.0 | 9.0 | 9.0 | 5.0 | 7.0 | 4.0 | 3.0 |
| | .125 | 6.0 | 6.0 | 7.0 | 2.0 | 9.0 | 9.0 | 4.0 | 7.0 | 2.0 | 2.0 |
| | .063 | 5.0 | 3.0 | 5.0 | 0.0 | 6.0 | 8.0 | 3.0 | 5.0 | 1.0 | 0.0 |
| 4-(4-Isopropyl-4-methyl-5-oxo-2-imidazolin-2-yl)-bicyclo[4.2.0]octa-1,3,5-triene-3-carboxylate | 2.000 | 9.0 | 7.0 | 8.0 | 9.0 | 2.0 | 9.0 | 7.0 | 8.0 | 2.0 | 0.0 |
| | 1.000 | 8.0 | 5.0 | 3.0 | 8.0 | 0.0 | 9.0 | 5.0 | 6.0 | 1.0 | 0.0 |
| | .500 | 7.0 | 4.0 | 0.0 | 8.0 | 0.0 | 9.0 | 2.0 | 3.0 | 0.0 | 0.0 |
| | .250 | 3.0 | 2.0 | 0.0 | 8.0 | 0.0 | 7.0 | 0.0 | 0.0 | 0.0 | 0.0 |
| | .125 | 2.0 | 0.0 | 0.0 | 2.0 | 0.0 | | 0.0 | 0.0 | 0.0 | 0.0 |
| | .063 | 0.0 | 0.0 | 0.0 | 0.0 | 0.0 | | 0.0 | 0.0 | 0.0 | 0.0 |
| Methyl 2-(4-isopropyl-4-methyl-5-oxo-2-imidazolin-2-yl)-3-(methylthio)benzoate | 2.000 | 0.0 | 0.0 | 0.0 | 0.0 | 0.0 | 7.0 | 9.0 | 3.0 | 0.0 | 0.0 |
| | 1.000 | 0.0 | 0.0 | 0.0 | 0.0 | 0.0 | 6.0 | 3.0 | 0.0 | 0.0 | 0.0 |
| | .500 | | 0.0 | 0.0 | 0.0 | 0.0 | 3.0 | 0.0 | 0.0 | 0.0 | 0.0 |
| | .250 | 0.0 | 0.0 | 0.0 | 0.0 | 0.0 | 0.0 | 0.0 | 0.0 | 0.0 | 0.0 |
| | .125 | 0.0 | 0.0 | | 0.0 | 0.0 | | | | 0.0 | 0.0 |
| | .063 | 0.0 | 0.0 | | | 0.0 | 0.0 | | | 0.0 | 0.0 |
| Methyl α-fluoro-6-(4-isopropyl-4-methyl-5-oxo-2-imidazolin-2-yl)-m-toluate | 2.000 | 2.0 | 0.0 | 0.0 | 9.0 | 0.0 | 0.0 | 0.0 | 0.0 | 0.0 | 0.0 |
| | 1.000 | 0.0 | 0.0 | 0.0 | 8.0 | 0.0 | 0.0 | 0.0 | 0.0 | 0.0 | 0.0 |
| | .500 | 0.0 | 0.0 | 0.0 | 7.0 | 0.0 | 0.0 | 0.0 | 0.0 | 0.0 | 0.0 |
| | .250 | 0.0 | 0.0 | 0.0 | 6.0 | 0.0 | 0.0 | 0.0 | 0.0 | 0.0 | 0.0 |
| | .125 | 0.0 | 0.0 | 0.0 | 2.0 | 0.0 | 0.0 | 0.0 | 0.0 | 0.0 | 0.0 |
| | .063 | 0.0 | 0.0 | 0.0 | 2.0 | 0.0 | 0.0 | 0.0 | 0.0 | 0.0 | 0.0 |
| 2-(4-Isopropyl-4-methyl-5-oxo-2-imidazolin-2-yl)-3-(methylthio)benzoic acid | 2.000 | 0.0 | 9.0 | 6.0 | 0.0 | 0.0 | 5.0 | 3.0 | 3.0 | 0.0 | 0.0 |
| | 1.000 | 0.0 | 7.0 | 3.0 | 0.0 | 0.0 | | 0.0 | 3.0 | 0.0 | 0.0 |
| | .500 | 0.0 | 7.0 | 0.0 | 0.0 | 0.0 | 0.0 | 0.0 | 0.0 | 0.0 | 0.0 |
| | .250 | 0.0 | 6.0 | 0.0 | 0.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| α-Fluoro-6-(4-isopropyl-4-methyl-5-oxo-2-imidazolin-2-yl)-m-toluic acid | 2.000 | 9.0 | 9.0 | 9.0 | 8.0 | 9.0 | 9.0 | 8.0 | 9.0 | 8.0 | 8.0 |
| | 1.000 | 8.0 | 9.0 | 9.0 | 6.0 | 7.0 | 9.0 | 8.0 | 8.0 | 6.0 | 7.0 |
| | .500 | 6.0 | 9.0 | 9.0 | 3.0 | | 9.0 | 7.0 | 8.0 | 5.0 | 5.0 |
| | .250 | 3.0 | 8.0 | 5.0 | 3.0 | 7.0 | 9.0 | 5.0 | 8.0 | 5.0 | 2.0 |
| | .125 | 0.0 | 7.0 | 5.0 | 2.0 | 0.0 | 8.0 | 5.0 | 7.0 | 2.0 | 2.0 |
| | 0.63 | 0.0 | 7.0 | 2.0 | 0.0 | 0.0 | 7.0 | 2.0 | 0.0 | 2.0 | 2.0 |
| Methyl α,α-difluoro-6-(4-isopropyl-4-methyl-5-oxo-2-imidazolin-2-yl)-m-anisate and methyl α,α-difluoro-2-(4-isopropyl-4-methyl-5-oxo-2-imidazolin-2-yl)-p-anisate | 2.000 | 8.0 | 9.0 | 5.0 | 8.0 | 9.0 | 7.0 | 6.0 | 7.0 | 3.0 | 2.0 |
| | 1.000 | 7.0 | 7.0 | 4.0 | 6.0 | 5.0 | 3.0 | 3.0 | 4.0 | 2.0 | 0.0 |
| | .500 | 5.0 | | 0.0 | 4.0 | 2.0 | 2.0 | 2.0 | 2.0 | 1.0 | 0.0 |
| | .250 | 3.0 | 2.0 | 0.0 | 3.0 | 0.0 | 0.0 | 0.0 | 0.0 | 0.0 | 0.0 |
| | .125 | 2.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| α,α-Difluoro-6-(4-isopropyl-4-methyl-5-oxo-2-imidazolin-2-yl)-m-anisic acid and α,α-difluoro-2-(4-isopropyl-4-methyl-5-oxo-2-imidazolin-2-yl)-p-anisic acid | 2.000 | 4.0 | 9.0 | 9.0 | 0.0 | 9.0 | 9.0 | 8.0 | 8.0 | 4.0 | 3.0 |
| | 1.000 | 3.0 | 9.0 | 4.0 | 0.0 | 9.0 | 9.0 | 5.0 | 5.0 | 3.0 | 3.0 |
| | .500 | 3.0 | 2.0 | 2.0 | 0.0 | 3.0 | 3.0 | 0.0 | 4.0 | 2.0 | 2.0 |
| | .250 | 2.0 | 0.0 | 0.0 | 0.0 | 0.0 | 0.0 | 0.0 | 0.0 | 1.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| Methyl α-fluoro-2-(4-isopropyl-4-methyl-5-oxo-2-imidazolin-2-yl)-p-toluate | 2.000 | 8.0 | 7.0 | 8.0 | 9.0 | 0.0 | 9.0 | 8.0 | 8.0 | 2.0 | 0.0 |
| | 1.000 | 7.0 | 5.0 | 5.0 | 9.0 | 0.0 | 8.0 | 5.0 | 6.0 | 1.0 | 0.0 |
| | .500 | 6.0 | 5.0 | 2.0 | 7.0 | 0.0 | 5.0 | 2.0 | 5.0 | 1.0 | 0.0 |
| | .250 | 3.0 | 2.0 | 0.0 | 0.0 | 0.0 | 2.0 | 0.0 | 2.0 | 0.0 | 0.0 |
| | .125 | 2.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| Methyl α,α,α-trifluoro-6-(4-isopropyl-4-methyl-5-oxo-2-imidazolin-2-yl)-m-anisate | 2.000 | 3.0 | 0.0 | 0.0 | 8.0 | 0.0 | 8.0 | 3.0 | 8.0 | 0.0 | 0.0 |
| | 1.000 | 0.0 | 0.0 | 0.0 | 8.0 | 0.0 | 7.0 | 2.0 | 8.0 | 0.0 | 0.0 |
| | .500 | 0.0 | 0.0 | 0.0 | 8.0 | 0.0 | 3.0 | 0.0 | 3.0 | 0.0 | 0.0 |
| | .250 | 0.0 | 0.0 | 0.0 | 3.0 | 0.0 | 0.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 0.0 |
| α,α,α-trifluoro-6-(4-isopropyl-4-methyl-5-oxo-2-imidazolin-2-yl)-m-anisic acid sodium sulfate | 2.000 | 3.0 | 0.0 | 3.0 | 2.0 | 9.0 | 9.0 | 5.0 | 3.0 | 4.0 | 6.0 |
| | 1.000 | 0.0 | 0.0 | 2.0 | 0.0 | 5.0 | 3.0 | 3.0 | 0.0 | 3.0 | 3.0 |
| | .500 | 0.0 | 0.0 | | 0.0 | 3.0 | 2.0 | 0.0 | 0.0 | 2.0 | 3.0 |
| | .250 | 0.0 | 0.0 | 0.0 | 0.0 | 0.0 | 0.0 | 0.0 | 0.0 | 2.0 | 0.0 |
| | .125 | 0.0 | 0.0 | 0.0 | 0.0 | 0.0 | 0.0 | 0.0 | 0.0 | 1.0 | 0.0 |
| | .063 | 0.0 | 0.0 | 0.0 | 0.0 | 0.0 | 0.0 | 0.0 | 0.0 | 1.0 | 0.0 |

What is claimed is:

1. A compound having the structure:

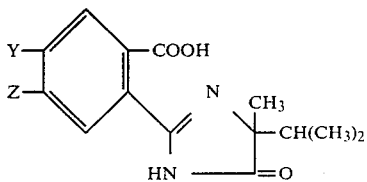

wherein Y and Z taken together are —(CH$_2$)n— where n=2–4 or —CH=CH$_2$—CH=CH$_2$.

2. A compound according to claim 1, 5,6,7,8-tetrahydro-3-(4-isopropyl-4-methyl-5-oxo-2-imidazolin-2-yl)-2-naphthoic acid.

3. A compound according to claim 1, 3-(4-isopropyl-4-methyl-5-oxo-2-imidazolin-2-yl)-2-naphthoic acid hydrochloride.

4. A compound according to claim 1, 4-(4-isopropyl-4-methyl-5-oxo-2-imidazolin-2-yl)bicyclo octa-1,3,5-triene-3-carboxylic acid.

5. A herbicidal composition comprising an inert diluent and a herbicidally effective amount of a compound having the structure:

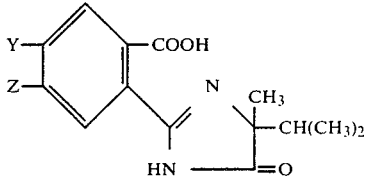

wherein Y and Z taken together are —(CH$_2$)n— where n=2–4 or —CH=CH$_2$—CH=CH$_2$—.

6. A method for the control of monocotyledonous and dicotyledonous annual, perennial and aquatic plant species comprising: applying to the foliage of the plants or to soil or water containing seeds or other propagating organs thereof, a herbicidally effective amount of a compound having a structure:

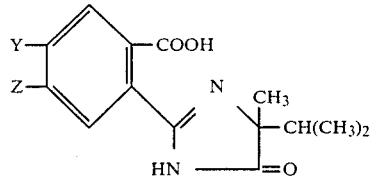

wherein Y and Z taken together are —(CH$_2$)n— where n=2–4 or —CH=CH$_2$—CH=CH$_2$.

7. A method according to claim 6, wherein said compound is applied to the foliage of undesirable plant species at a rate sufficient to provide from 0.016 to 4.0 kg/ha of said compound.

8. A method according to claim 6, wherein said compound is applied to soil containing seeds or other propagating organs of undesirable plants at a rate sufficient to provide from about 0.016 to 4.0 kg/ha of said compound.

9. A method according to claim 6, wherein the compound is
5,6,7,8-tetrahydro-3-(4-isopropyl-4-methyl-5-oxo-2-imidazolin-2-yl)-2-naphthoic acid;
3-(4-isopropyl-4-methyl-5-oxo-2-imidazolin-2-yl)-2-naphthoic acid hydrochloride; or
4-(4-isopropyl-4-methyl-5-oxo-2-imidazolin-2-yl)bicyclo[4.2.0]octa-1,3,5-triene-3-carboxylic acid.

* * * * *